United States Patent
Shin et al.

(10) Patent No.: US 11,332,598 B2
(45) Date of Patent: May 17, 2022

(54) ACETYLATED LACTIDE OLIGOMER-BASED PLASTICIZER, METHOD OF PREPARING SAME AND PLA RESIN COMPOSITION CONTAINING SAME

(71) Applicant: KOREA RESEARCH INSTITUTE OF CHEMICAL TECHNOLOGY, Daejeon (KR)

(72) Inventors: Jihoon Shin, Daejeon (KR); Haemin Jeong, Daejeon (KR); Nam-Kyun Kim, Daejeon (KR); Young-Wun Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/811,903

(22) Filed: Mar. 6, 2020

(65) Prior Publication Data

US 2020/0325301 A1    Oct. 15, 2020

(30) Foreign Application Priority Data

Apr. 12, 2019 (KR) .................... 10-2019-0042823
Feb. 14, 2020 (KR) .................... 10-2020-0018440

(51) Int. Cl.
C08K 5/11 (2006.01)
C07C 67/465 (2006.01)
C07C 69/34 (2006.01)

(52) U.S. Cl.
CPC .............. *C08K 5/11* (2013.01); *C07C 67/465* (2013.01); *C07C 69/34* (2013.01)

(58) Field of Classification Search
CPC ......... C08K 5/11; C08G 63/08; C07C 67/465; C07C 69/34; C08L 101/00
See application file for complete search history.

(56) References Cited

U.S. PATENT DOCUMENTS

| 9,290,613 B2 * | 3/2016 | Uyama .................. C08G 63/08 |
| 2005/0192388 A1 * | 9/2005 | Craun ...................... C08K 5/10 524/284 |

FOREIGN PATENT DOCUMENTS

| KR | 10-1502796 | * | 3/2015 | |
| KR | 10-1502796 B1 | | 3/2015 | |
| KR | 10-1875130 B1 | * | 8/2018 | ............... C08G 3/08 |

OTHER PUBLICATIONS

KR 101875130 (B1), Lee, et al., PLA PLA composition having improved mechanical property, English translation 18 pages (Year: 2018).*

(Continued)

*Primary Examiner* — Yate' K Cutliff
(74) *Attorney, Agent, or Firm* — Lewis Roca Rothgerber Christie LLP

(57) ABSTRACT

Disclosed herein is an acetylated lactide oligomer-based plasticizer and a method of preparing the same having improved thermal stability, enhanced plasticity and excellent compatibility with a resin, the method, including: (a) synthesizing a lactide oligomer through ring-opening polymerization (ROP) of an initiator and lactide; (b) putting acetic anhydride into the lactide oligomer and performing acetylation; and (c) removing acetic acid generated in step (b) and unreacted acetic anhydride.

11 Claims, 21 Drawing Sheets
(14 of 21 Drawing Sheet(s) Filed in Color)

(56) References Cited

OTHER PUBLICATIONS

Substances Part A, Poison list 1: List of toxic substances; Table A, Toxic list—Directory of toxic substances, Substances sorted by name, Publisher, Federal Office of Health, Bern,Switzerland; aethyl-(O-(O-(O-acetyllactyl)-lactyl)-lactyl)-lactat); issue 8, Jan. 2004, p. 9 (33), 465 pages (Year: 2004).*

Robert, J.L., et al., Ring-opening polymerization of lactide to from a biodegradable polymer, Green Chemistry, Journal of Chemical Education, vol. 85, No. 2, pp. 258-260 (Year: 2008).*

KR10-1502796, Yeong-Un Kim, et al. PVC Resin Plasticizer Composition Containing Low Molecular Weight Lactide Oligomer, English translation, 10 pages (Year: 2015).*

Office action for Korean patent Application No. 10-2020-0018440, dated May 7, 2021, 8 pages.

\* cited by examiner

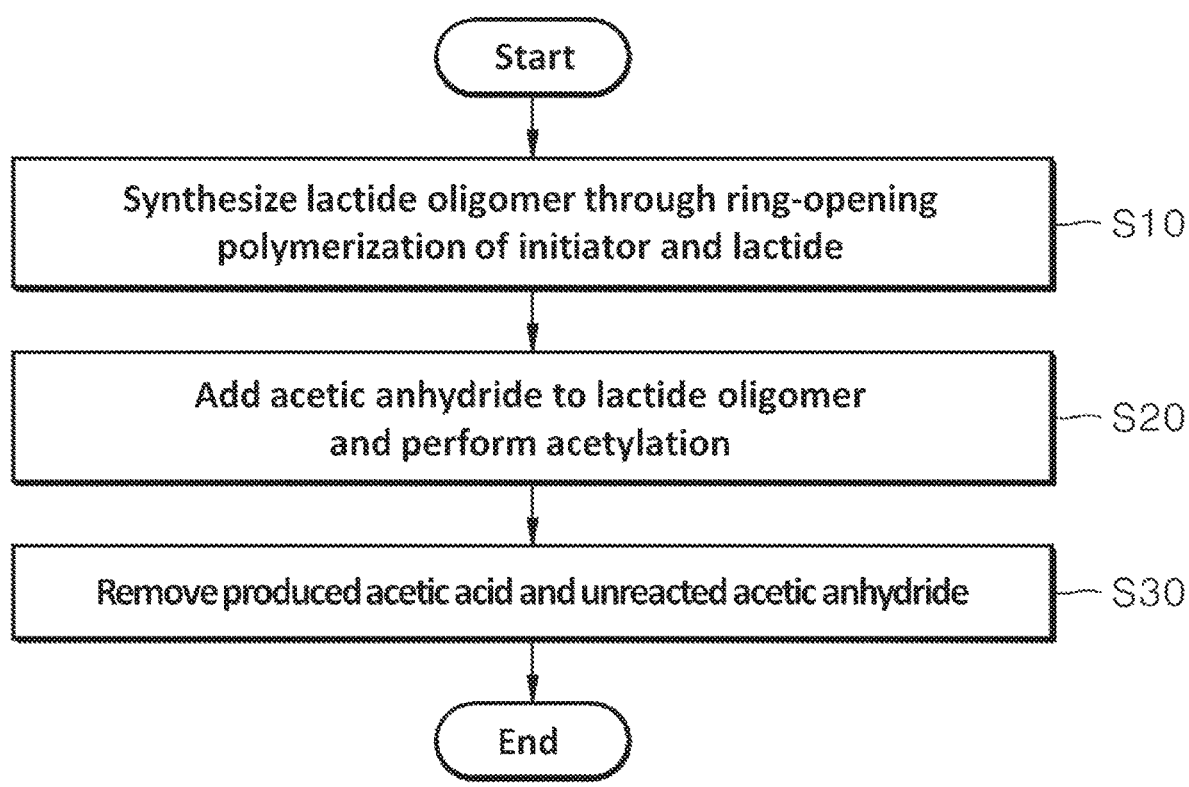
[FIG. 1]

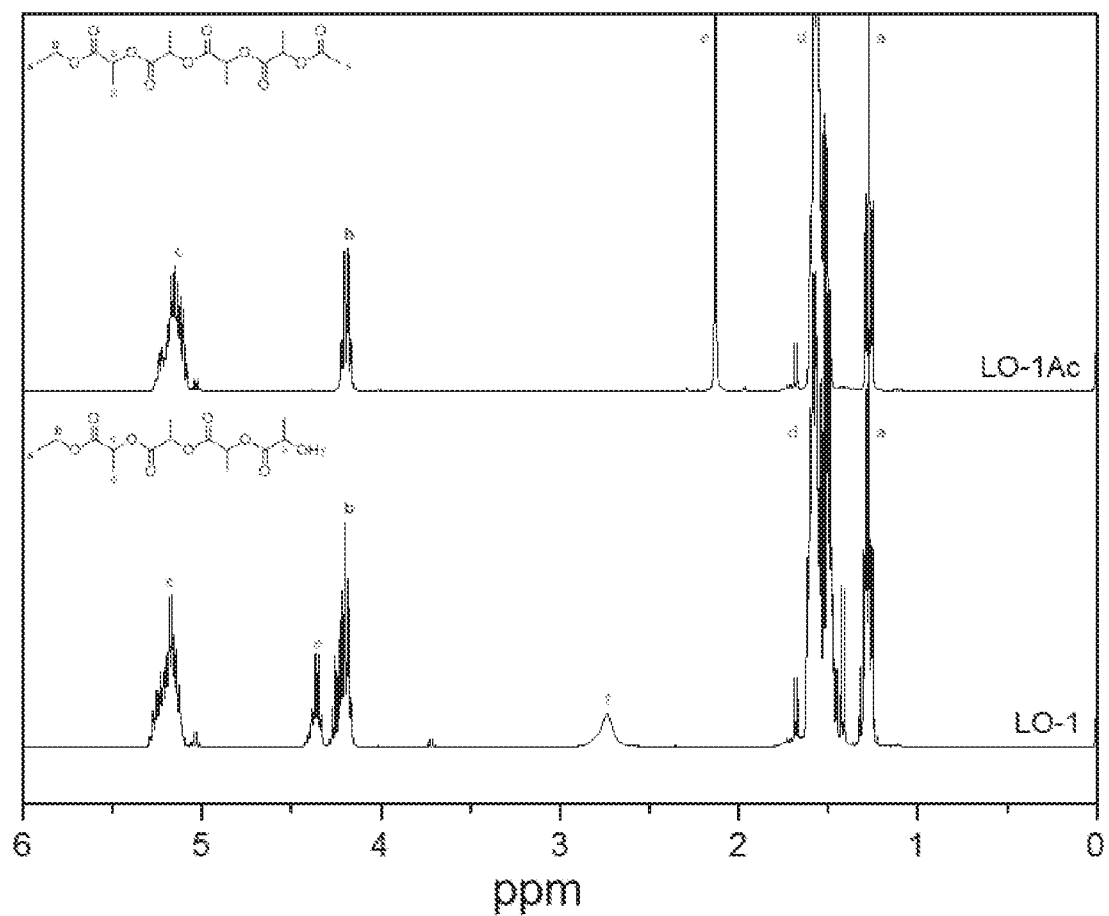
[FIG. 2]

[FIG. 3]
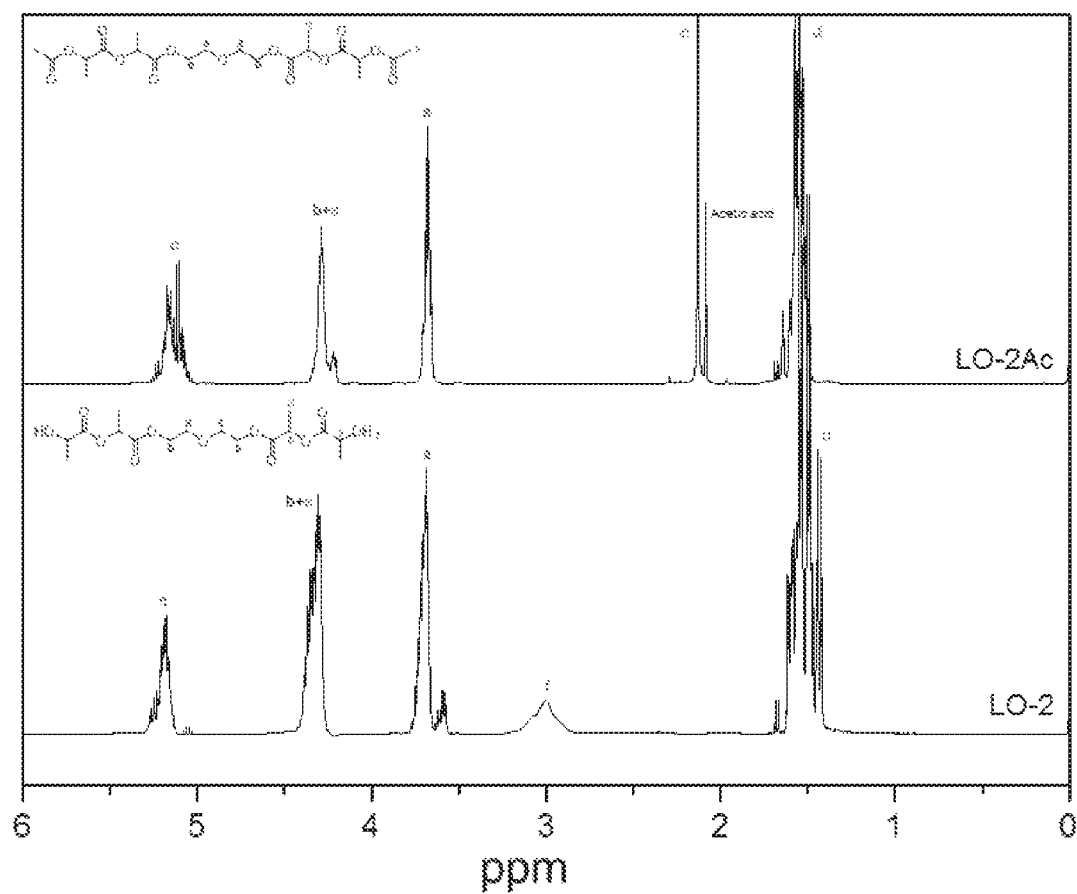

[FIG. 4]
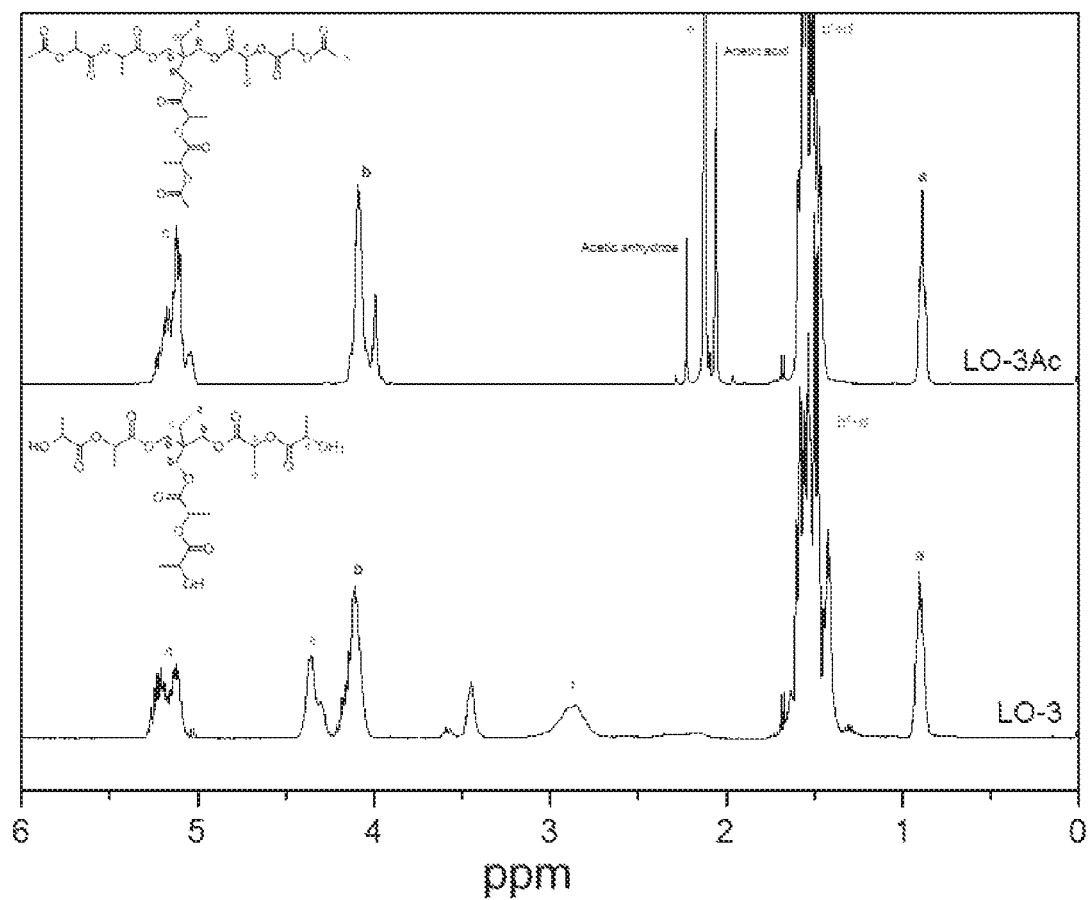

[FIG. 5]
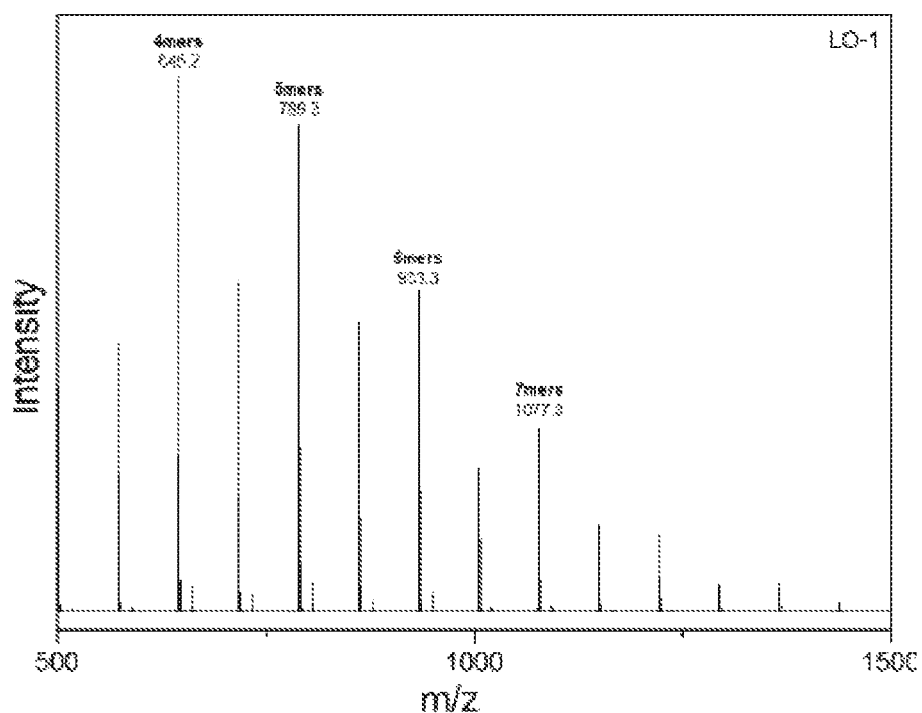
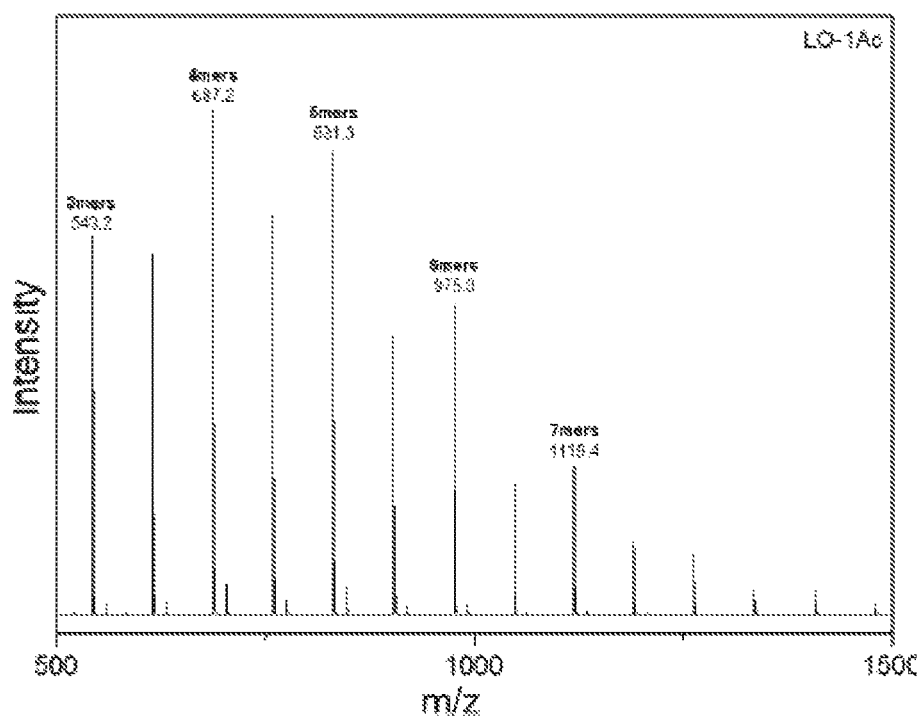

[FIG. 6]
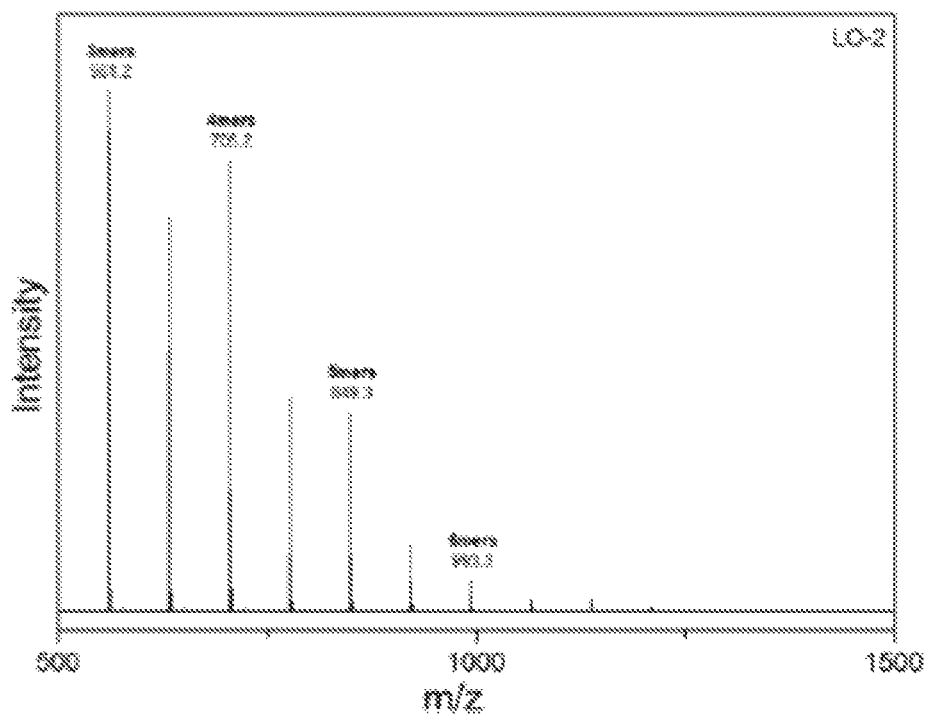
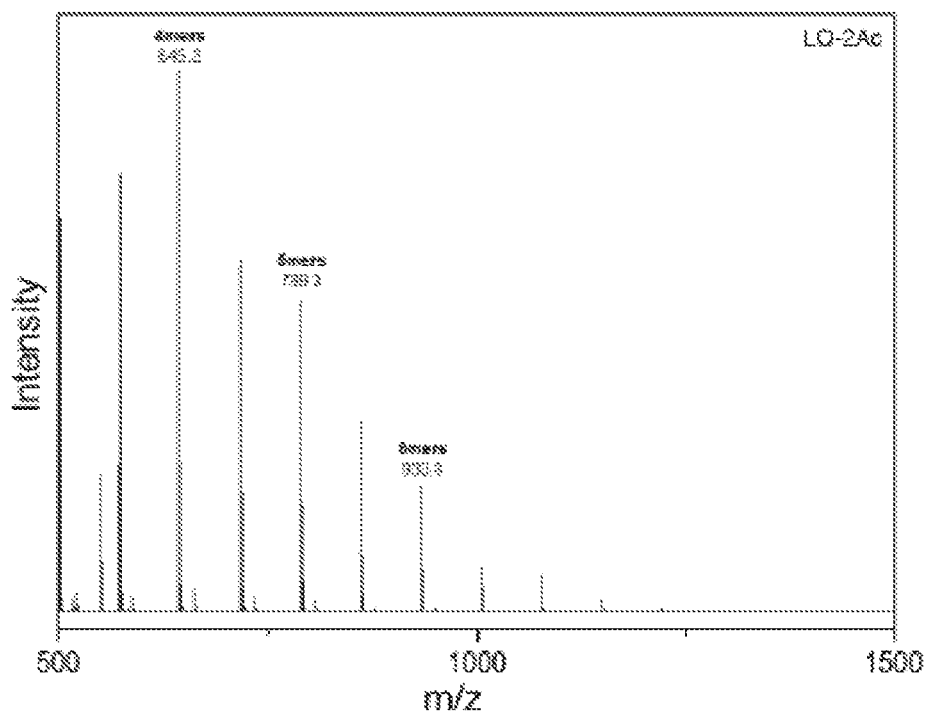

[FIG. 7]
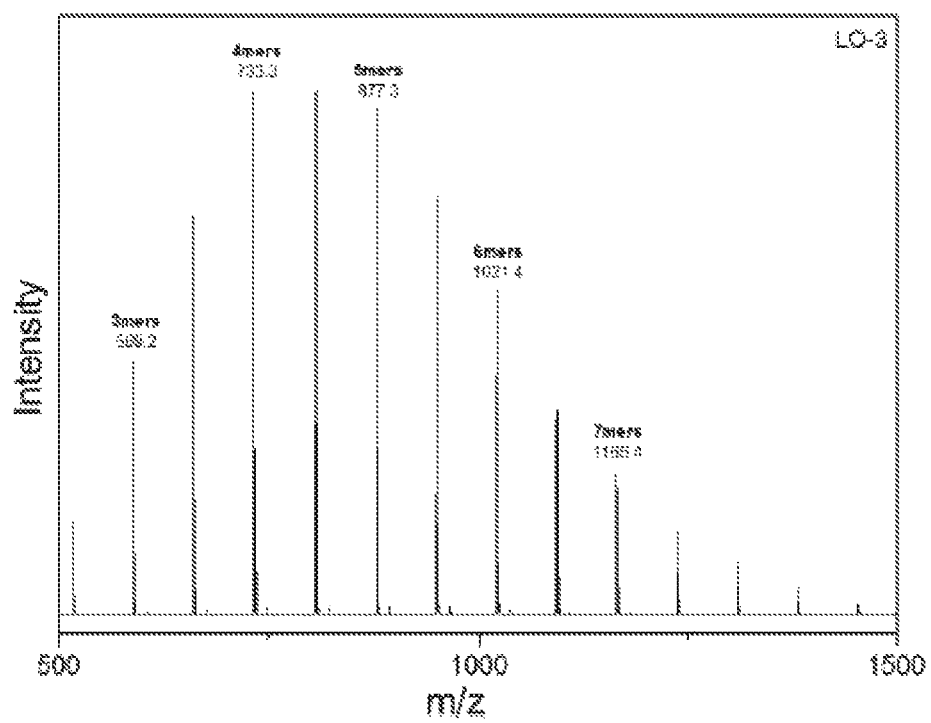
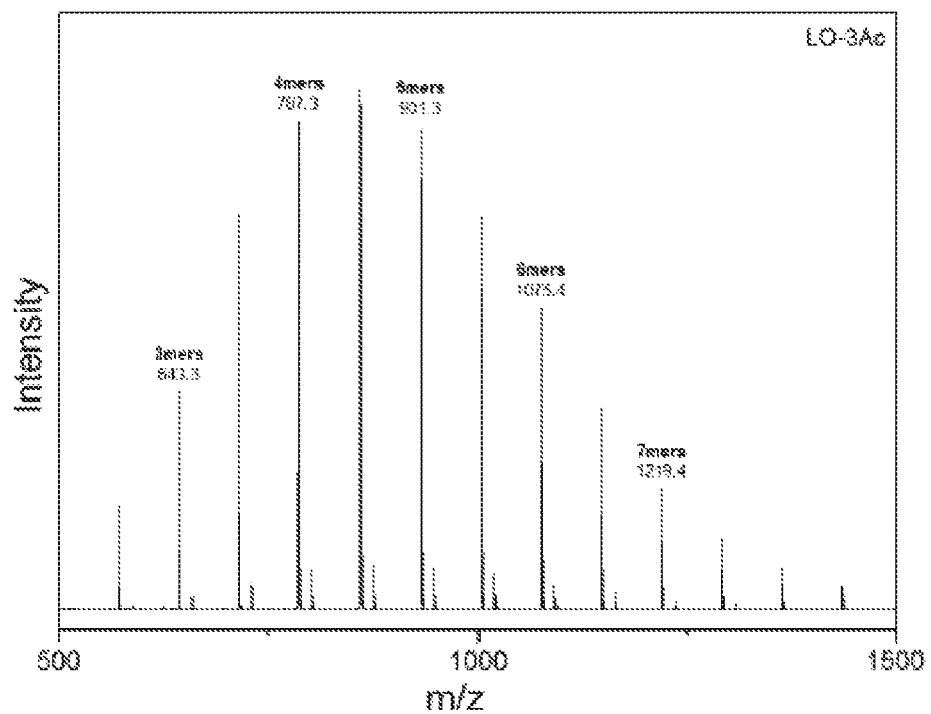

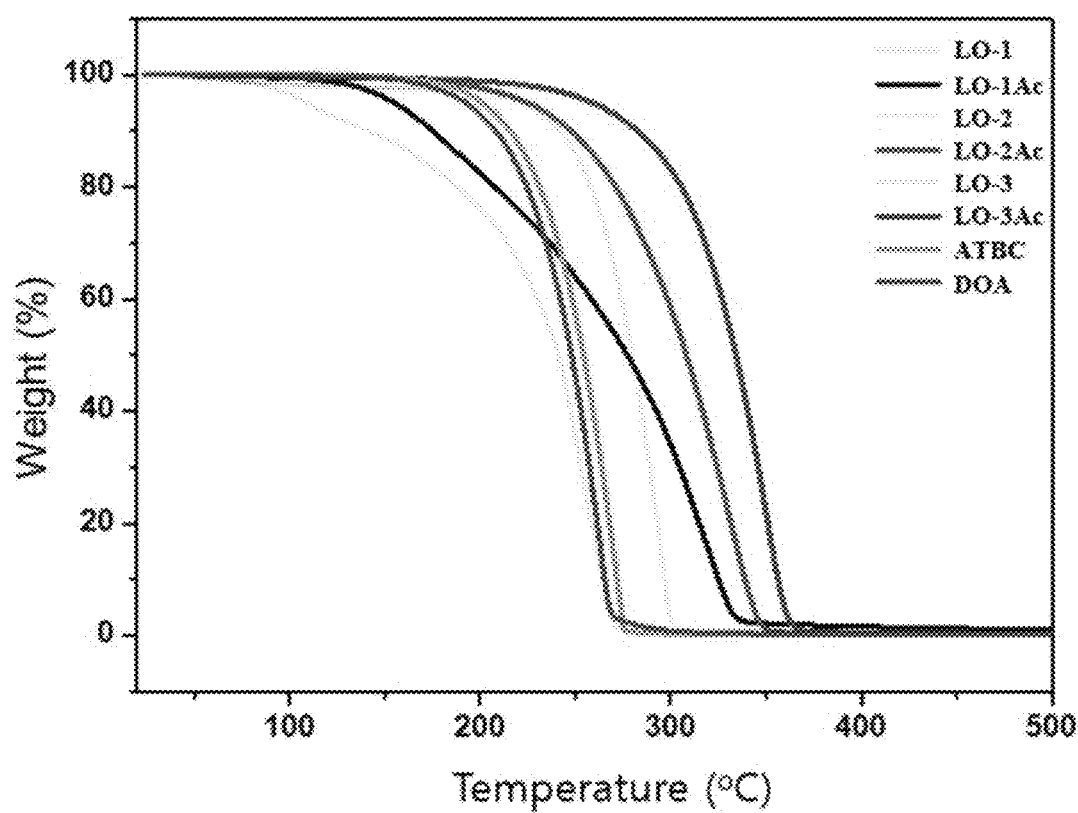
[FIG. 8]

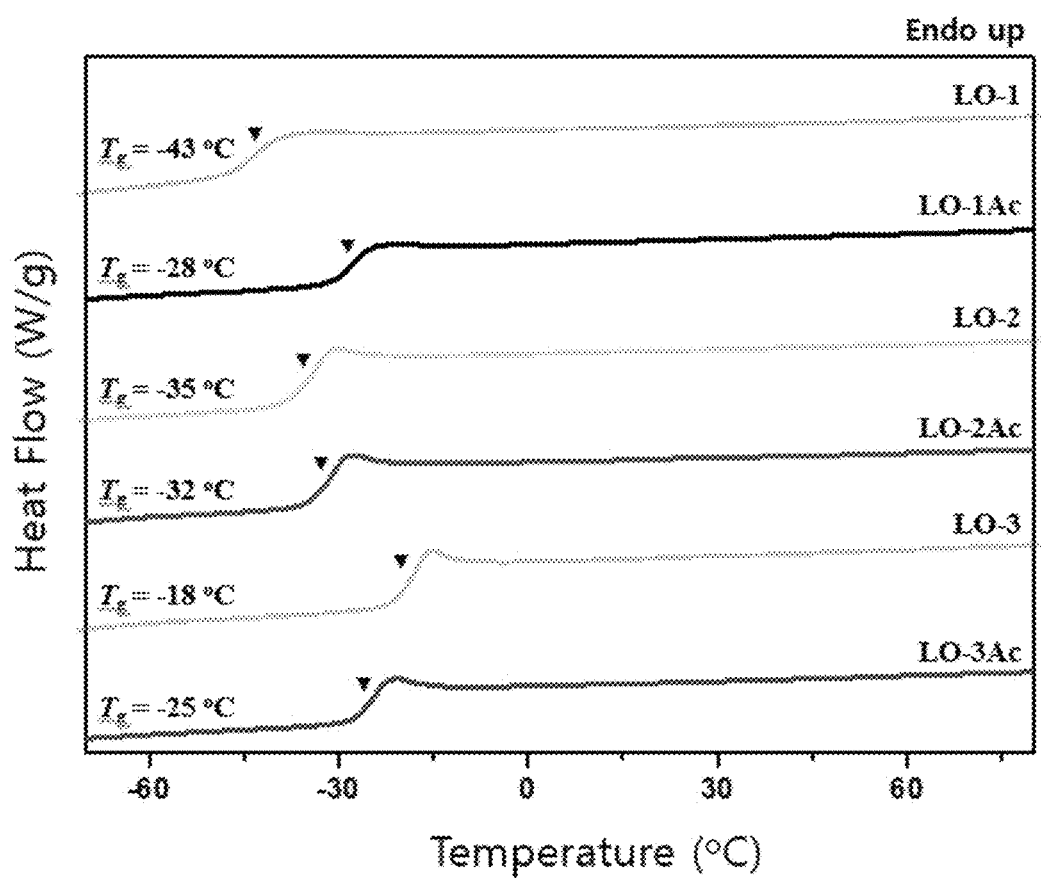
[FIG. 9]

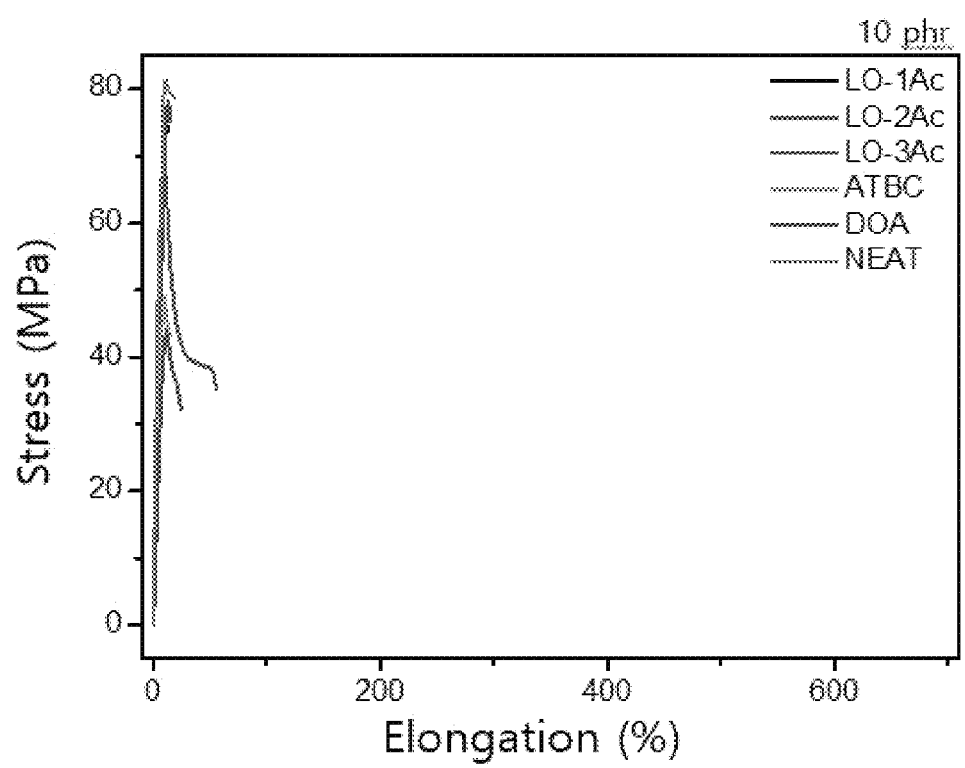
[FIG. 10]

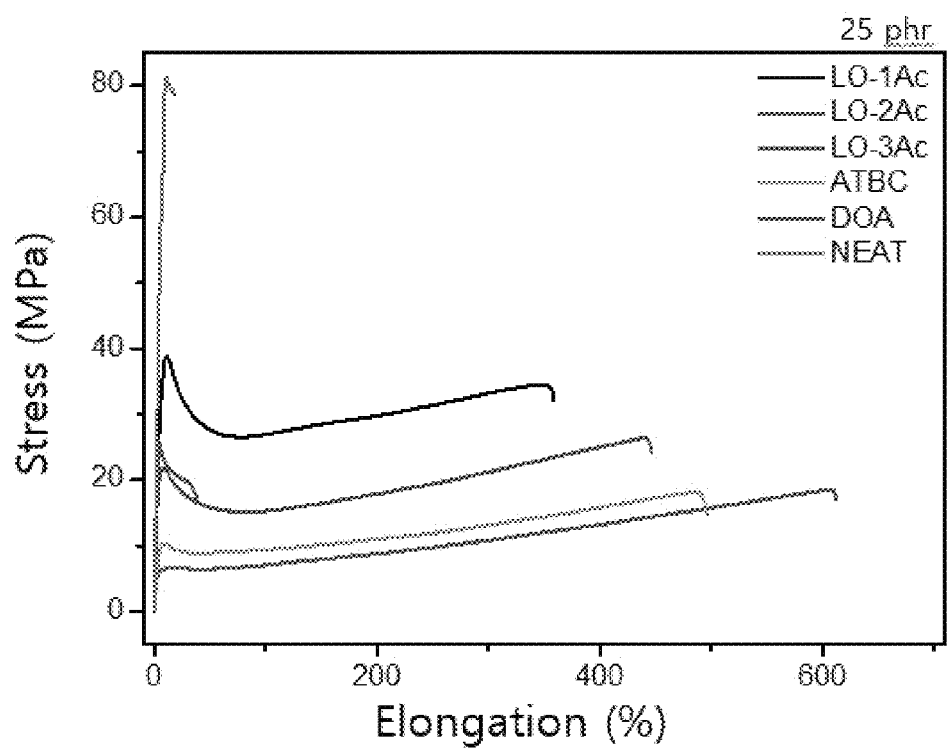
[FIG. 11]

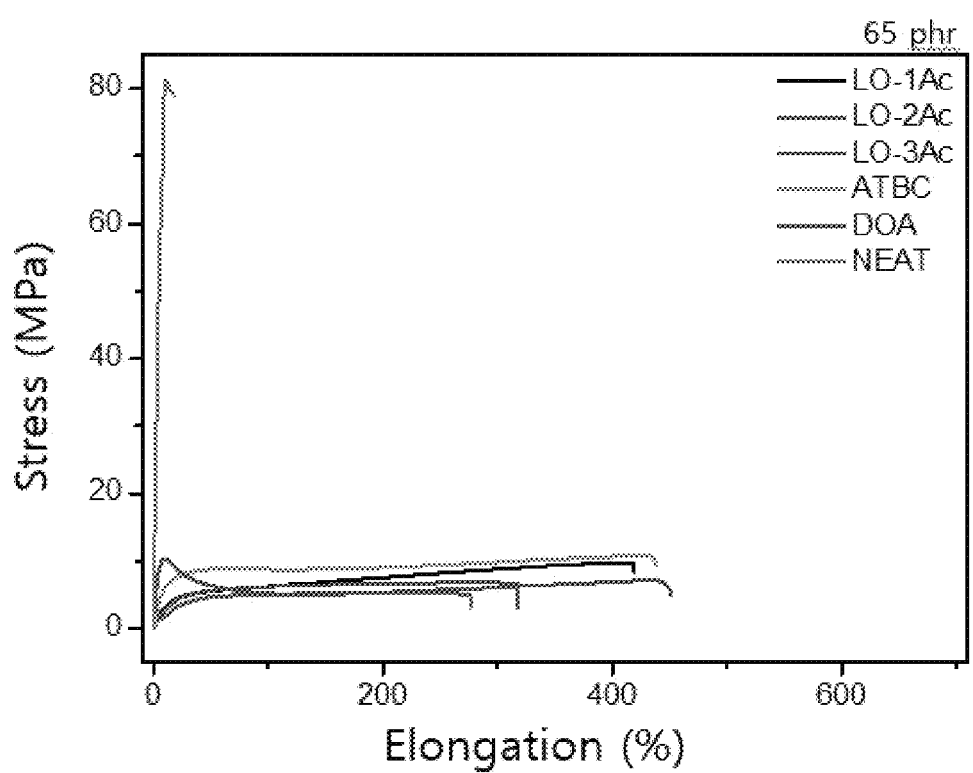
[FIG. 12]

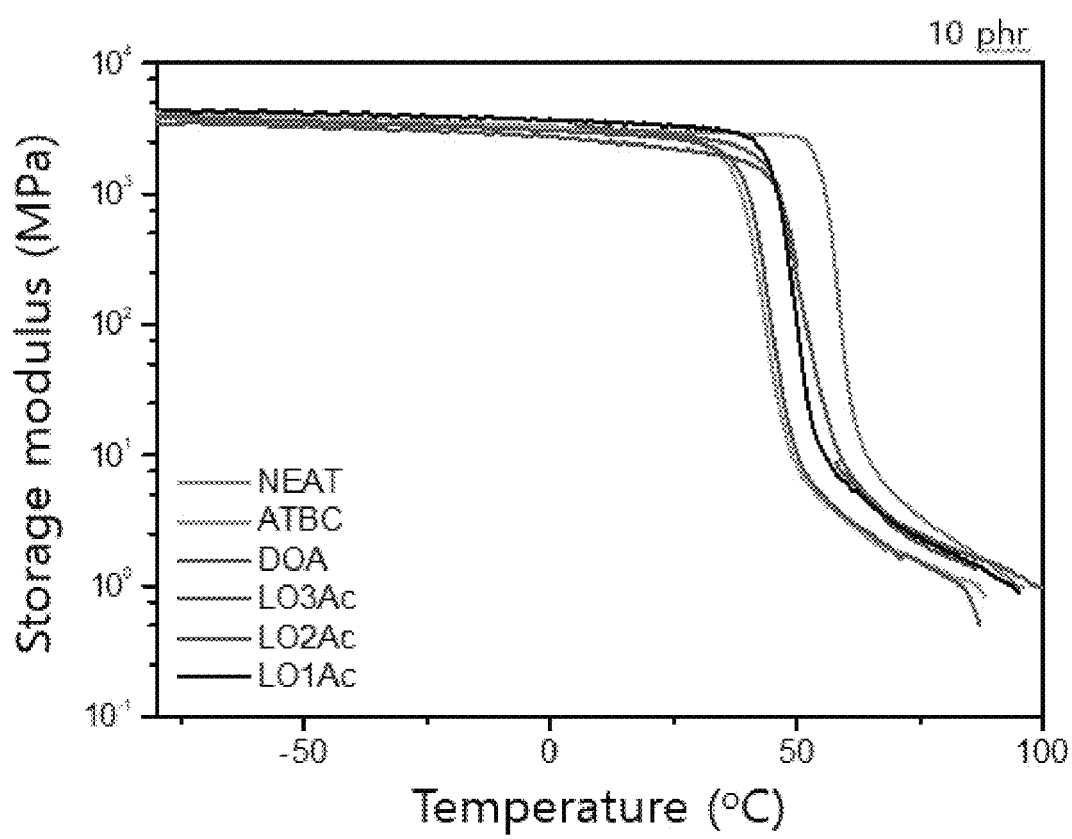
[FIG. 13]

[FIG. 14]
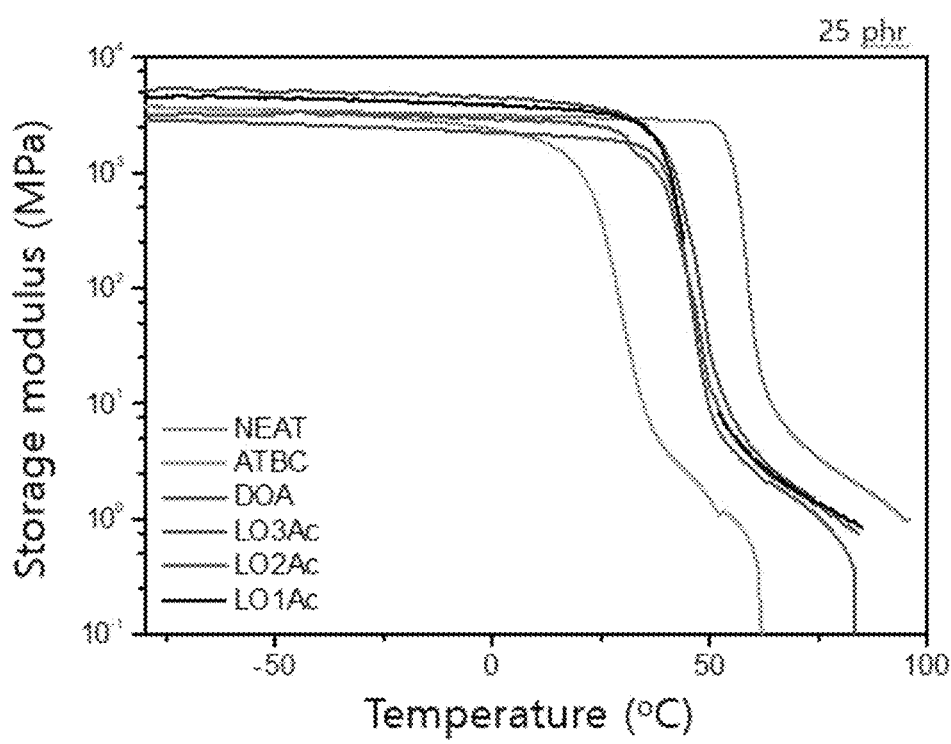

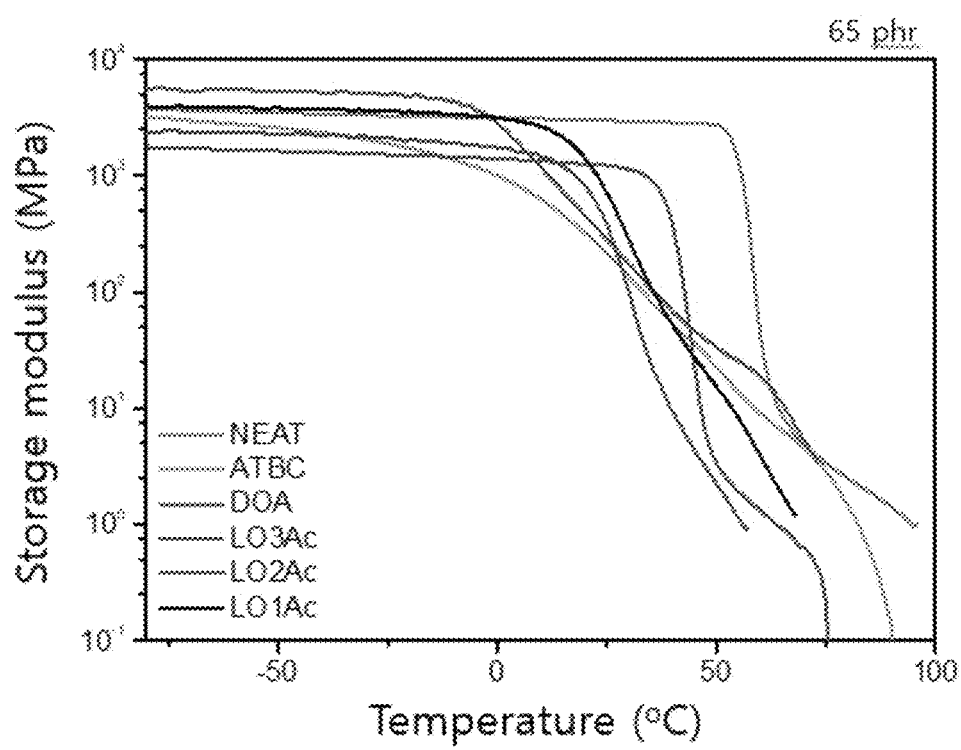
[FIG. 15]

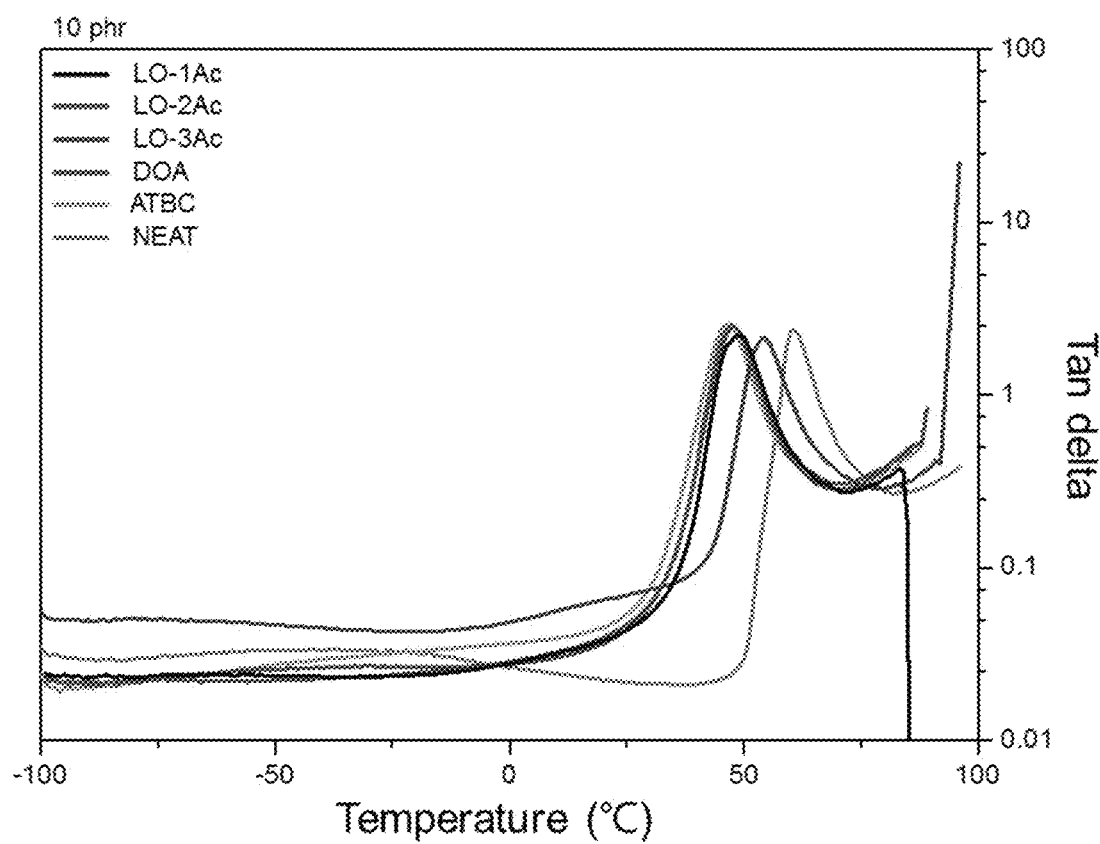
[FIG. 16]

[FIG. 17]
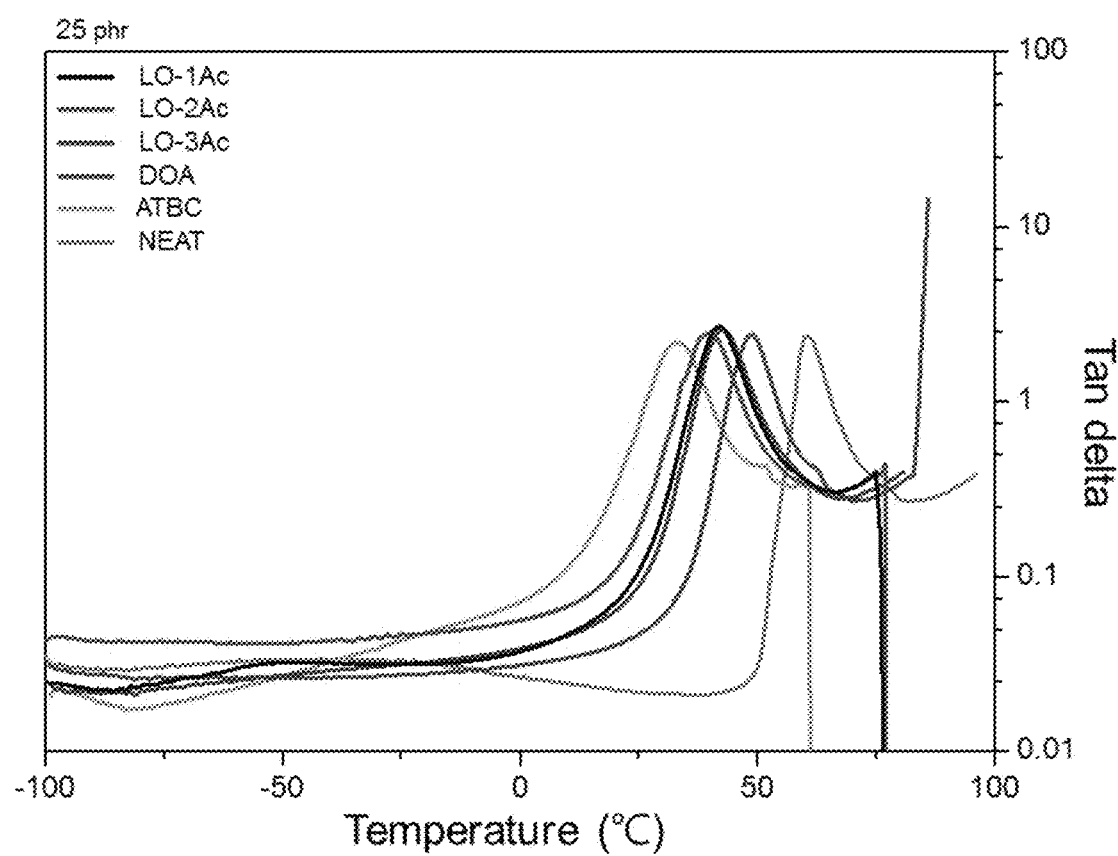

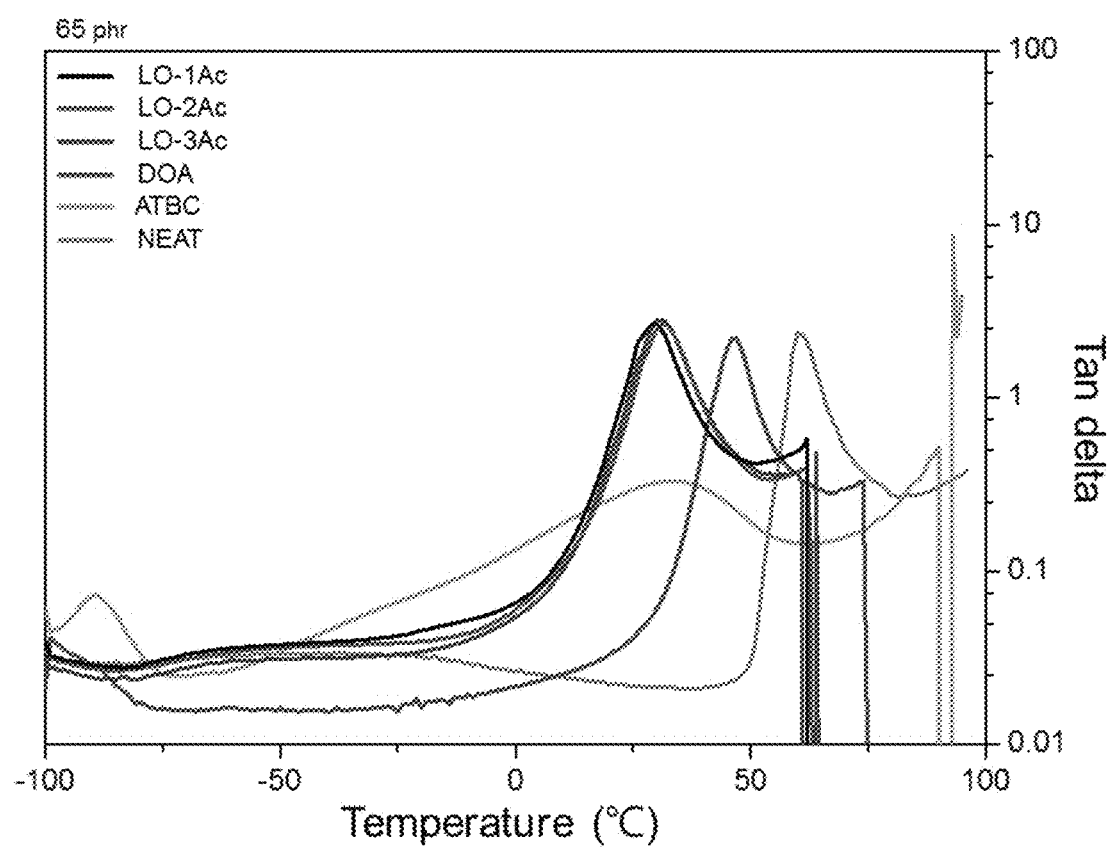
[FIG. 18]

[FIG. 19]
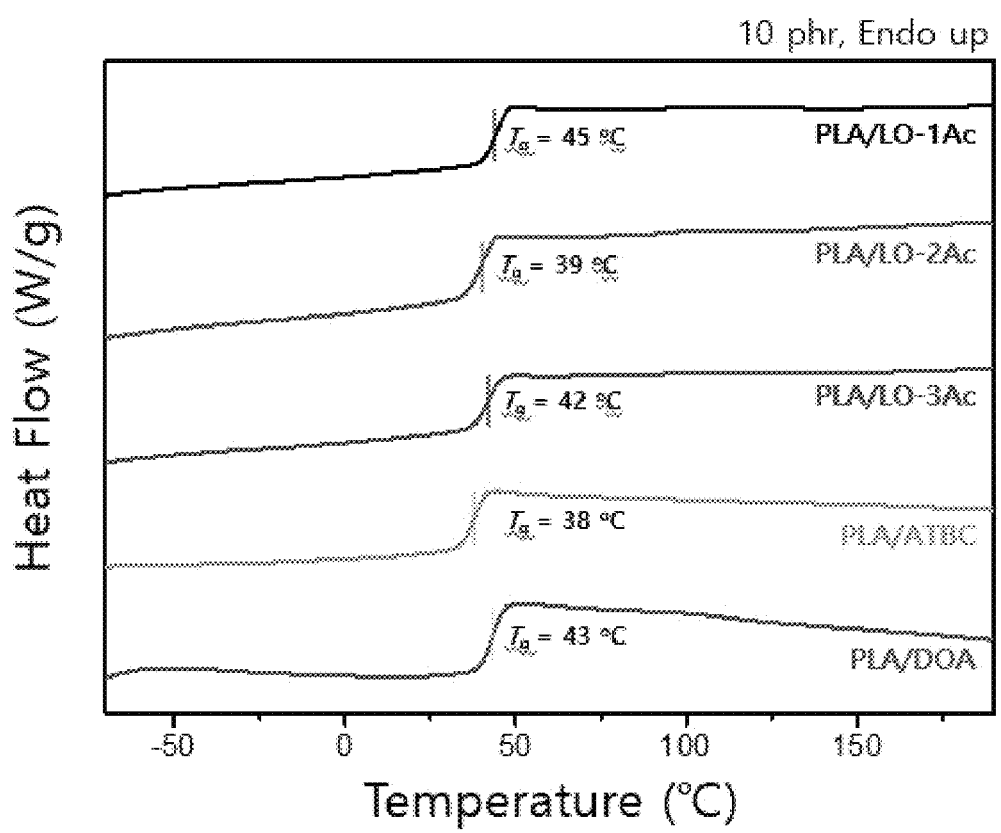

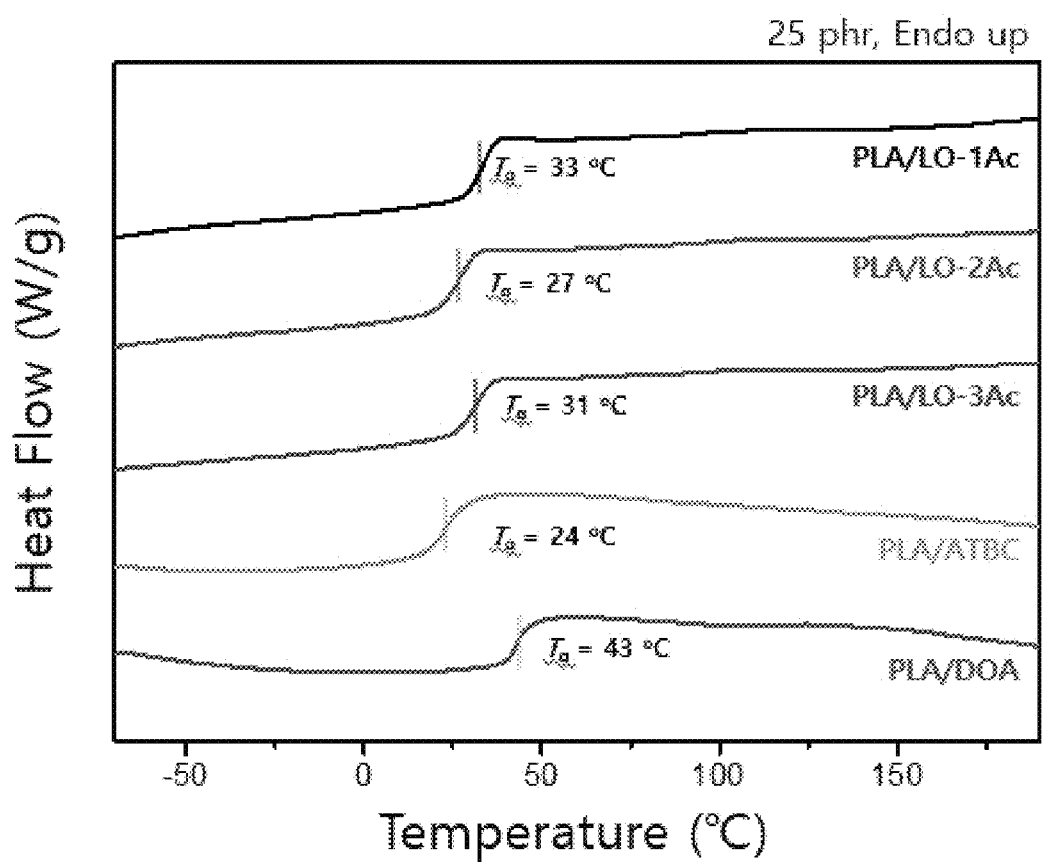
[FIG. 20]

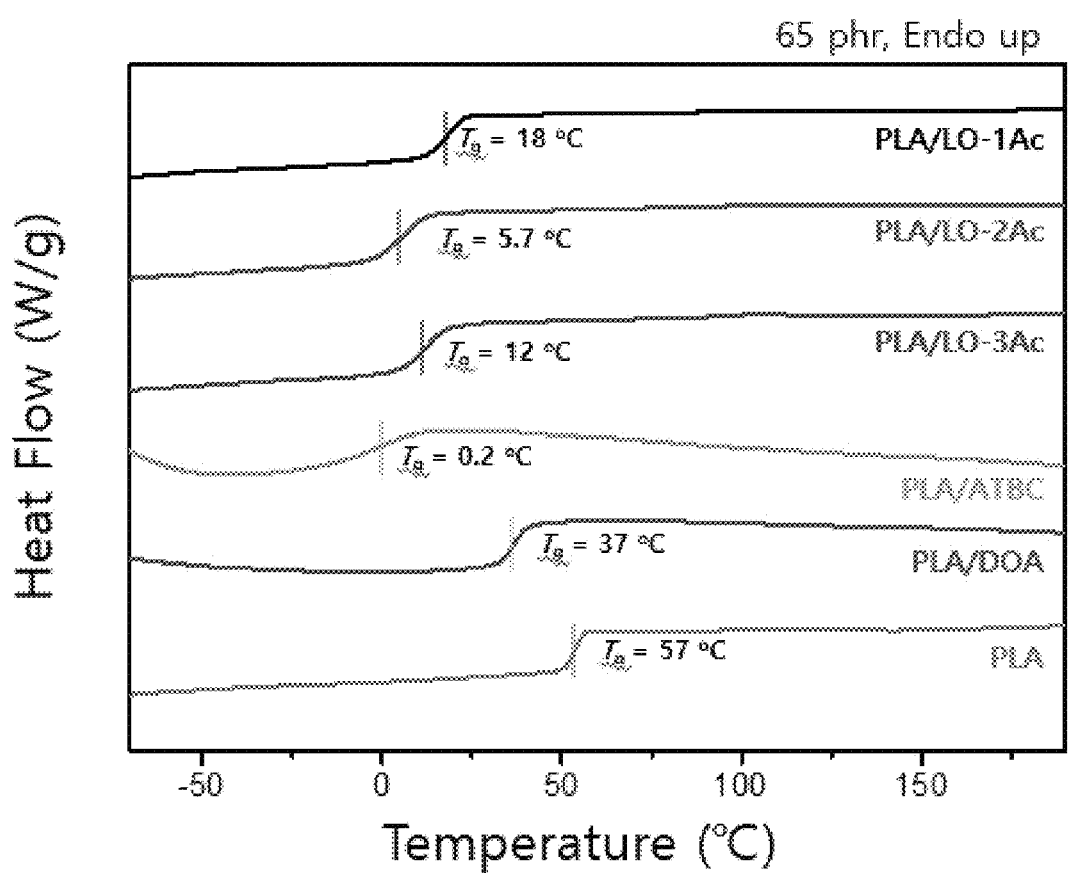
[FIG. 21]

ACETYLATED LACTIDE OLIGOMER-BASED PLASTICIZER, METHOD OF PREPARING SAME AND PLA RESIN COMPOSITION CONTAINING SAME

CROSS-REFERENCE TO RELATED APPLICATION

This application claims priority to and the benefit of Korean Patent Application No. 10-2019-0042823, filed in Korea on Apr. 12, 2019 and Korean Patent Application No. 10-2020-0018440, filed in Korea on Feb. 14, 2020, the disclosures of which are incorporated herein by reference in its entirety.

BACKGROUND

1. Field

The present disclosure relates to an acetylated lactide oligomer-based plasticizer, a method of preparing the same, and a PLA resin composition containing the same, and, more particularly, to an acetylated lactide oligomer-based plasticizer having excellent thermal stability and plasticity, a method of preparing the same, and a PLA resin composition containing the same.

2. Background

At a time when physical properties such as compatibility and biodegradability are important factors in terms of environmental protection, there is a growing need for a biodegradable resin that decomposes in the natural environment in the polymer chemistry field.

Accordingly, research into poly lactic acid, a copolymer of lactic acid and another aliphatic hydroxy carboxylic acid, polyester derived from aliphatic polyhydric alcohol and aliphatic polyvalent carboxylic acid, and the like has been actively performed.

Polylactic acid (PLA), which is an environmentally friendly resin derived from agricultural products that are somewhat immune from resource scarcity, can be cheaply produced in large numbers using fermentation of D, L-lactide. PLA has glass transition temperature of 60° C. and has physical properties similar to those of existing plastics. PLA is also a material that is approved by the Food and Drug Administration (FDA) and is used in a variety of fields including packaging, medicine, agriculture, pharmacy and the like, thanks to its biodegradability and biocompatibility.

PLA, however, is highly crystalline and has a rigid molecular structure. Accordingly, it is solid, is easily broken, has low flexibility, and has low workability. Thus, PLA itself cannot be used as a film or a packaging material and the like in need of flexibility.

Methods of soft-nitriding PLA may include a method of adding a plasticizer, a method of blending a soft-nitrided polymer, a method of copolymerization and the like. The method of blending a soft-nitrided polymer is limited only to a blend of a biodegradable resin such as polybutylene succiate and the like when it comes to biodegradability. To give sufficient flexibility to PLA, a large amount of resins has to be added. As a result, properties of PLA cannot be sufficiently revealed and PLA is vulnerable to damage. In the method of copolymerization, physical properties of a copolymer such as a melting point, thermal resistance and the like can be changed depending on crystallinity and low glass transition point of PLA.

When a plasticizer is added to PLA, the plasticizer reduces contact between molecules in the resin. Accordingly, workability, flexibility and durability of the resin can be improved, and, in some cases, product costs can be reduced. An ideal eco-friendly plasticizer has to be derived from renewable sources and has to have biodegradability. Additionally, like an existing plasticizer, it has to have high compatibility with a resin, to have high chemical stability when processed, and to ensure excellent exudation resistance.

Research into eco-friendly plasticizers such as a vegetable oil-based eco-friendly plasticizer, a succinic acid-based eco-friendly plasticizer, an isosorbide plasticizer and the like has been so far performed. However, unlike an existing phthalate-based plasticizer, they have limited physical properties.

As described above, plasticizers added to complement and improve physical properties of an eco-friendly biodegradable resin have been developed. However, they have low workability and limited mechanical properties and the like. Accordingly, a plasticizer that can overcome the above-describe drawbacks and can have excellent biodegradability, mechanical properties and compatibility is required. Additionally, there is room for improvement in the use of an eco-friendly biodegradable resin in a wide range of industrial fields by applying the plasticizer to the eco-friendly biodegradable resin.

SUMMARY

The present disclosure is directed to an acetylated lactide oligomer-based plasticizer that has improved thermal stability and has improved plasticity.

The present disclosure is also directed to an acetylated lactide oligomer-based plasticizer that has excellent compatibility with a PLA resin and is environmentally friendly.

As a means to achieve the above-described objectives, provided is a method of preparing an acetylated lactide oligomer-based plasticizer, comprising: (a) synthesizing a lactide oligomer through ring-opening polymerization (ROP) of an initiator and lactide; (b) putting acetic anhydride into the lactide oligomer and performing acetylation; and (c) removing acetic acid generated in step (b) and unreacted acetic anhydride.

In step (a), the initiator may be any one selected from a group consisting of 1,1,1-tris(hydroxymethyl)propane, diethylene glycol, and ethanol.

Step (a) may be carried out at 100 to 120° C. for two to six hours.

In step (a), a catalyst of the ring-opening polymerization may include tin(II) 2-ethylhexanoate.

Step (b) may be carried out at 80 to 120° C. for 40 to 60 hours.

Further, provided is an acetylated lactide oligomer-based plasticizer that is manufactured by acetylating a lactide oligomer synthesized through ring-opening polymerization (ROP) of an initiator and lactide and that is expressed as any one of the following chemical formulas 1 to 3.

[Chemical formula 1]

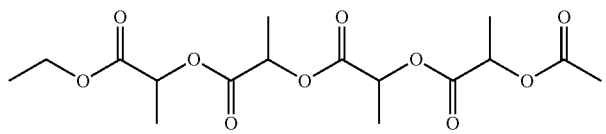

[Chemical formula 2]

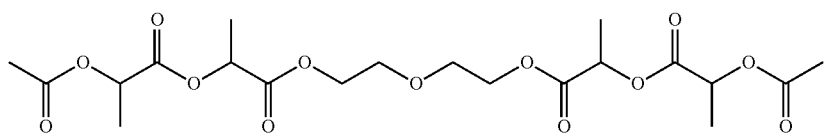

[Chemical formula 3]

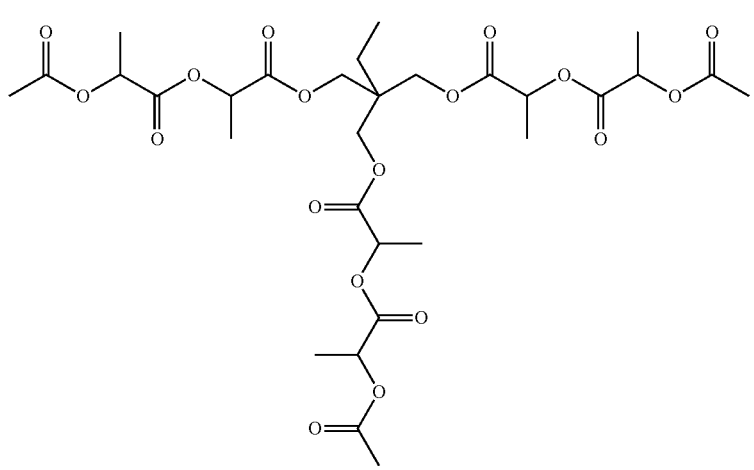

The initiator may be any one selected from a group consisting of 1,1,1-tris(hydroxymethyl)propane, diethylene glycol, and ethanol.

A catalyst of the ring-opening polymerization may include tin(II) 2-ethylhexanoate.

The ring-opening polymerization may be carried out at 100 to 120° C. for two to six hours.

The acetylation may be carried out at 80 to 120° C. for 40 to 60 hours.

Furthermore, provided is a PLA resin composition that includes a poly lactic acid (PLA) resin, and any one selected from acetylated lactide oligomer-based plasticizers expressed as the following chemical formulas 1 to 3.

[Chemical formula 1]

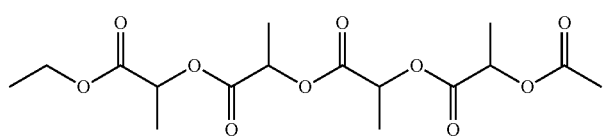

[Chemical formula 2]

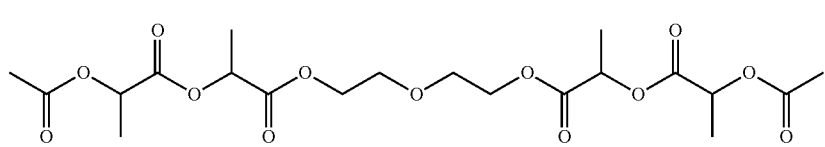

-continued

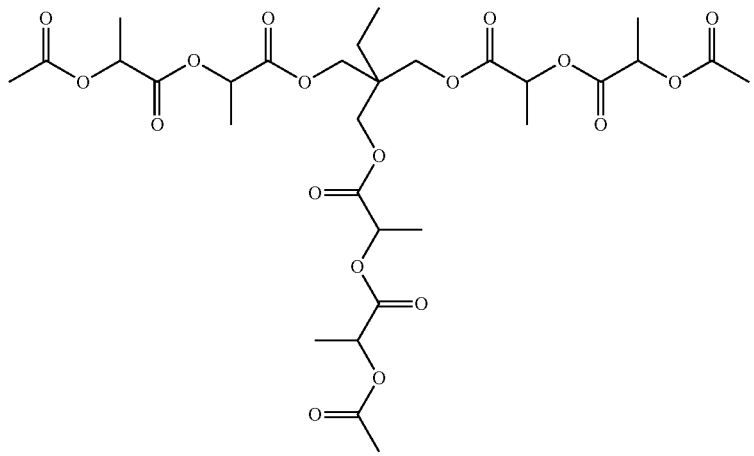

[Chemical formula 3]

The plasticizer may be contained in a range of 25 to 70 phr with respect to the PLA resin composition.

According to the method of preparing an acetylated lactide oligomer-based plasticizer, a terminal of a hydroxy group of a plasticizer is replaced with an acetyl group through acetylation, thereby improving thermal stability.

The acetylated lactide oligomer-based plasticizer prepared according to the method has more excellent plasticity and compatibility with a PLA resin than a commercial plasticizer.

BRIEF DESCRIPTION OF THE DRAWINGS

Embodiments are described in detail with reference to the following drawings, wherein:

The patent or application file contains at least one drawing executed in color. Copies of this patent or patent application publication with color drawing(s) will be provided by the Office upon request and payment of the necessary fee.

FIG. 1 is a flow chart illustrating a method of preparing an exemplary acetylated lactide oligomer-based plasticizer;

FIG. 2 is a graph illustrating results of comparison of $^1$H-NMR before and after acetylation of a hydroxy group terminal of a lactide oligomer according to embodiment 1;

FIG. 3 is a graph illustrating results of comparison of $^1$H-NMR before and after acetylation of a hydroxy group terminal of a lactide oligomer according to embodiment 2;

FIG. 4 is a graph illustrating results of comparison of $^1$H-NMR before and after acetylation of a hydroxy group terminal of a lactide oligomer according to embodiment 3;

FIG. 5 is a graph illustrating results of comparison of MALDI-TOF-MS before and after acetylation of a hydroxy group terminal of a lactide oligomer according to embodiment 1;

FIG. 6 is a graph illustrating results of comparison of MALDI-TOF-MS before and after acetylation of a hydroxy group terminal of a lactide oligomer according to embodiment 2;

FIG. 7 is a graph illustrating results of comparison of MALDI-TOF-MS before and after acetylation of a hydroxy group terminal of a lactide oligomer according to embodiment 3;

FIG. 8 is a graph illustrating results of comparison of analyses of plasticizers of embodiments 1 to 3 and analyses of DOA and ATBC plasticizers using thermogravimetric analysis (TGA);

FIG. 9 is a graph illustrating results of comparison of evaluations of thermal properties of plasticizers of embodiments 1 to 3 and evaluations of thermal properties of DOA and ATBC plasticizers using differential scanning calorimetry (DSC);

FIG. 10 is a graph illustrating results of comparison of stress-strain curves of embodiments 4 to 6 in which 10 phr of a plasticizer was added, a PLA sample of comparative examples 1 and 2 in which 10 phr of a plasticizer was added, and a PLA sample in which a plasticizer was not added;

FIG. 11 is a graph illustrating results of comparison of stress-strain curves of embodiments 4 to 6 in which 25 phr of a plasticizer was added, a PLA sample of comparative examples 1 and 2 in which 25 phr of a plasticizer was added, and a PLA sample in which a plasticizer was not added;

FIG. 12 is a graph illustrating results of comparison of stress-strain curves of embodiments 4 to 6 in which 65 phr of a plasticizer was added, a PLA sample of comparative examples 1 and 2 in which 65 phr of a plasticizer was added, and a PLA sample in which a plasticizer was not added;

FIG. 13 is a graph illustrating results of comparison of storage modulus (G') of embodiments 4 to 6 in which 10 phr of a plasticizer was added, storage modulus (G') of a PLA sample of comparative examples 1 and 2 in which 10 phr of a plasticizer was added, and storage modulus (G') of a PLA sample in which a plasticizer was not added;

FIG. 14 is a graph illustrating results of comparison of storage modulus (G') of embodiments 4 to 6 in which 25 phi of a plasticizer was added, storage modulus (G') of a PLA sample of comparative examples 1 and 2 in which 25 phr of a plasticizer was added, and storage modulus (G') of a PLA sample in which a plasticizer was not added;

FIG. 15 is a graph illustrating results of comparison of storage modulus (G') of embodiments 4 to 6 in which 65 phi of a plasticizer was added, storage modulus (G') of a PLA sample of comparative examples 1 and 2 in which 65 phr of a plasticizer was added, and storage modulus (G') of a PLA sample in which a plasticizer was not added;

FIG. 16 is a graph illustrating results of comparison of tan δ of embodiments 4 to 6 in which 10 phr of a plasticizer was added, tan δ of a PLA sample of comparative examples 1 and 2 in which 10 phr of a plasticizer was added, and tan δ of a PLA sample in which a plasticizer was not added;

FIG. 17 is a graph illustrating results of comparison of tan δ of embodiments 4 to 6 in which 25 phr of a plasticizer was added, tan δ of a PLA sample of comparative examples 1 and 2 in which 25 phr of a plasticizer was added, and tan δ of a PLA sample in which a plasticizer was not added;

FIG. 18 is a graph illustrating results of comparison of tan δ of embodiments 4 to 6 in which 65 phr of a plasticizer was added, tan δ of a PLA sample of comparative examples 1 and 2 in which 65 phr of a plasticizer was added, and tan δ of a PLA sample in which a plasticizer was not added;

FIG. 19 is a graph illustrating results of comparison of analyses of embodiments 4 to 6 in which 10 phr of a plasticizer was added, a PLA sample of comparative examples 1 and 2 in which 10 phr of a plasticizer was added, and a PLA sample in which a plasticizer was not added, using differential scanning calorimetry (DSC);

FIG. 20 is a graph illustrating results of comparison of analyses of embodiments 4 to 6 in which 25 phr of a plasticizer was added, a PLA sample of comparative examples 1 and 2 in which 25 phi of a plasticizer was added, and a PLA sample in which a plasticizer was not added, using differential scanning calorimetry (DSC); and FIG. 21 is a graph illustrating results of comparison of analyses of embodiments 4 to 6 in which 65 phr of a plasticizer was added, a PLA sample of comparative examples 1 and 2 in which 65 phi of a plasticizer was added, and a PLA sample in which a plasticizer was not added, using differential scanning calorimetry (DSC).

DETAILED DESCRIPTION

FIG. 1 is a flow chart illustrating a method of preparing an exemplary acetylated lactide oligomer-based plasticizer.

Referring to FIG. 1, an exemplary acetylated lactide oligomer-based plasticizer is prepared in steps of (a) synthesizing a lactide oligomer through ring-opening polymerization (ROP) of an initiator and lactide; (b) performing acetylation by adding acetic anhydride to the lactide oligomer; and (c) removing acetic acid produced in step (b) and unreacted acetic anhydride.

Below, preferred embodiments of the present disclosure are described with reference to the accompanying drawings.

Advantages and features of the disclosure, and a method of achieving the same may be clearly understood from the following embodiments that are specifically described with reference to the accompanying drawings.

The present disclosure, however, may be implemented in various different forms, and should not be construed as being limited only to the embodiments set forth herein. Rather, these embodiments are provided as examples so that the present disclosure will be thorough and complete and that the scope of the disclosure will be fully conveyed to one having ordinary skill in the art to which the disclosure pertains. The present invention should be defined by the scope of the appended claims.

In describing the disclosure, detailed description of known technologies and the like in relation to the disclosure is omitted if it is deemed to make the gist of the present disclosure unnecessarily vague.

Below, a method of preparing an exemplary acetylated lactide oligomer-based plasticizer is described.

FIG. 1 is a flow chart illustrating a method of preparing an exemplary acetylated lactide oligomer-based plasticizer.

Referring to FIG. 1, an exemplary acetylated lactide oligomer-based plasticizer is prepared in steps of (a) synthesizing a lactide oligomer through ring-opening polymerization (ROP) of an initiator and lactide; (b) performing acetylation by adding acetic anhydride to the lactide oligomer; and (c) removing acetic acid produced in step (b) and unreacted acetic anhydride.

First, an initiator and lactide are ring-opening polymerized (S10).

In the above step, a catalysis is put into lactide, and a lactide oligomer is synthesized through ring-opening polymerization.

In the above-described ring-opening polymerization, ethanol, diethylene glycol, and 1,1,1-tris(hydroxymethyl) propane and the like may be used as an initiator but the initiator is not limited.

To perform the above-described ring-opening polymerization, the lactide and the initiator are put into a reactor, a catalyst is added, and then heating and stirring is performed.

The catalyst may be tin(II) 2-ethylhexanoate ($Sn(Oct)_2$), and dioctyltin dilaurate, and, preferably, may be tin(II) 2-ethylhexanoate ($Sn(Oct)_2$).

The catalyst may be added in the form of a solution that is dissolved in a solvent. When the catalyst is added in the form of a solution that is dissolved in a solvent, the solvent may be first removed before the lactide and the initiator react.

The solvent may include an organic solvent such as an aromatic solvent including toluene, benzene, xylene and the like, an alkyl halide solvent including methylene chloride, chloroform and the like, an aliphatic solvent including hexane and the like, an organic solvent including tetrahydrofuran, acetone, dioxane and the like, and the like, and, preferably, may include toluene, benzene, acetone or tetrahydrofuran.

The above step may be carried out for two to six hours at 100 to 120° C. Under the above-described conditions, a relatively small amount of catalysts may be used. Under the above-described conditions, 0.002 to 0.003 mole of the catalyst may be added with respect to 1 mole of the initiator, and, preferably, 0.0025 mole of the catalyst may be added with respect to 1 mole of the initiator.

Next, acetic anhydride is put into the produced lactide oligomer, and acetylation is performed (S20).

In the above step, a hydroxy group (—OH) of a terminal of the lactide oligomer is replaced with an acetyl group (—$COCH_3$) through acetylation.

The acetylation step may be carried out through solution condensation polymerization or bulk condensation polymerization.

At the time of polycondensation, a metallic catalyst may be used to facilitate the reaction. The metallic catalysts may include alkali metal such as lithium, sodium, potassium and the like, or may include oxides of alkali metal, hydroxides of alkali metal, chlorides of alkali metal, and the like. The metallic catalyst, for example, may include at least one selected from a group consisting of magnesium acetate, potassium acetate, calcium acetate, zinc acetate, manganese acetate, lead acetate, antimony acetate, and cobalt acetate.

Acid anhydride used in the above step may include at least one compound selected from a group consisting of acetic anhydride, diphenyl carbonate, and benzyl acetate, and, preferably, may include acetic anhydride.

One to four moles of the acid anhydride may be used with respect to a total content of one mole of the hydroxy group included in the lactide oligomer. When an amount of the acid anhydride used in the acetylation is within the above-described range, the used lactide oligomer may be sufficiently acetylated, and only a small amount of the used acid anhydride does not react. Accordingly, the unreacted acid anhydride may be readily removed.

The acetylation may be performed at 80 to 120° C. and may be preferably performed at 100° C. When a temperature of the reaction is 80° C. or higher, a hydroxy group of the terminal of the lactide oligomer may be sufficiently transformed into an acetyl group. When a temperature of the reaction is above 120° C., an amount of byproducts may increase.

Additionally, the reaction may be performed for 40 to 60 hours and may be preferably performed for 42 hours. When the reaction is performed for less than 40 hours, the reaction may not be readily caused, and, when the reaction is performed for more than 60 hours, an amount of byproducts may increase.

Finally, acetic acid generated in the acetylation and unreacted acetic anhydrides are removed, and then an acetylated lactide oligomer-based plasticizer is obtained (S30).

The exemplary acetylated lactide oligomer-based plasticizer prepared may be expressed as the following chemical formulas 1 to 3.

[Chemical formula 1]

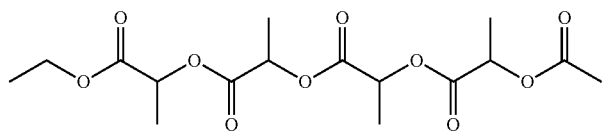

[Chemical formula 2]

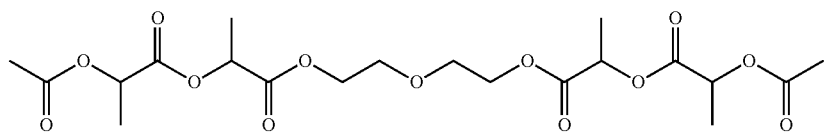

[Chemical Formula 3]

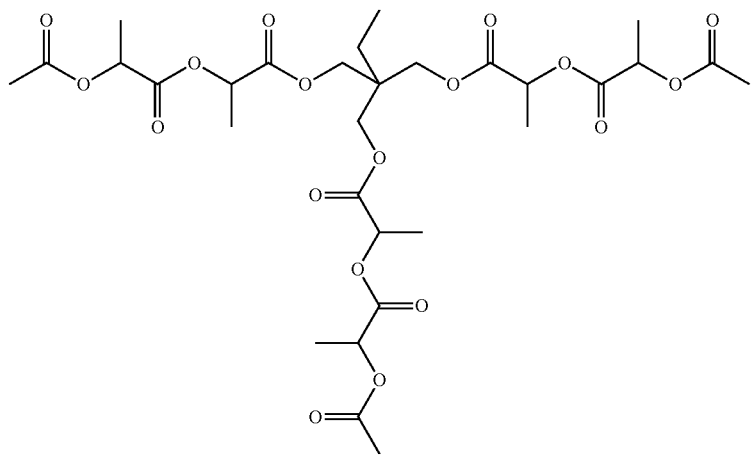

According to another aspect of the present disclosure, provided is an acetylated lactide oligomer-based plasticizer prepared by acetylating a lactide oligomer synthesized through ring-opening polymerization (ROP) of an initiator and lactide and, and the acetylated lactide oligomer-based plasticizer is expressed as any one of the following chemical formulas 1 to 3

[Chemical Formula 1]

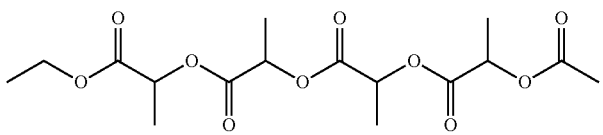

[Chemical Formula 2]

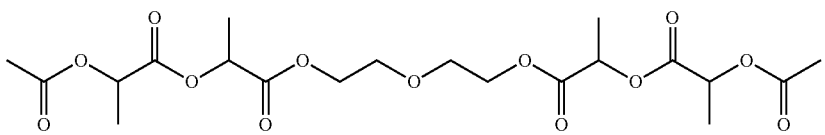

[Chemical Formula 3]

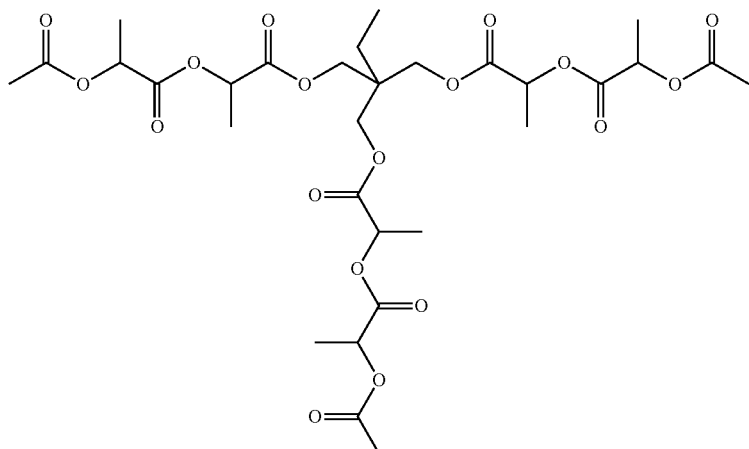

The initiator may be any one selected from a group consisting of 1,1,1-tris(hydroxymethyl)propane, diethylene glycol, and ethanol.

In the ring-opening polymerization, tin(II) 2-ethylhexanoate may be used as a catalyst.

The ring-opening polymerization may be performed at 100 to 120° C. for two to six hours. Under the conditions, a relatively small amount of the catalyst may be used. Under the above-described conditions, 0.002 to 0.003 mole of the catalyst may be added with respect to 1 mole of the initiator, and, preferably, 0.0025 mole of the catalyst may be added with respect to 1 mole of the initiator.

The acetylation may be performed at 80 to 120° C. and may be preferably performed at 100° C. When a temperature of the reaction is 80° C. or higher, a hydroxy group of the terminal of the lactide oligomer may be sufficiently transformed into an acetyl group. When a temperature of the reaction is above 120° C., an amount of byproducts may increase.

Additionally, the reaction may be performed for 40 to 60 hours and may be preferably performed for 42 hours. When the reaction is performed for less than 40 hours, the reaction may not be readily caused, and, when the reaction is performed for more than 60 hours, an amount of byproducts may increase.

The exemplary plasticizer may have excellent compatibility with a PLA resin, and may have excellent thermal stability through acetylation in which a hydroxy group of the terminal of the plasticizer is replaced with an acetyl group. Further, the exemplary plasticizer may have improved mechanical properties as the exemplary plasticizer has more excellent elongation and tensile strength than a commercial plasticizer through the acetylation.

Furthermore, the acetylated lactide oligomer-based plasticizer may maintain storage modulus unlike a commercial plasticizer, thereby ensuring excellent plasticity.

According to yet another aspect of the present disclosure, provided is a PLA resin composition including a poly lactic acid (PLA) resin, and any one selected from the acetylated lactide oligomer-based plasticizers expressed as the following chemical formulas 1 to 3.

[Chemical Formula 1]

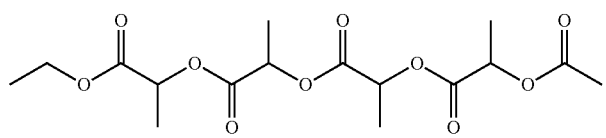

[Chemical Formula 2]

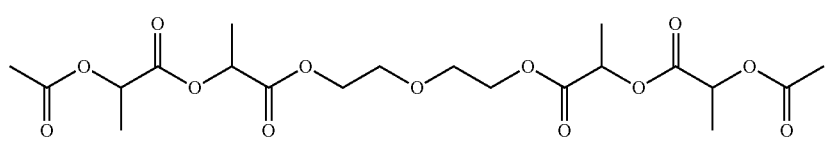

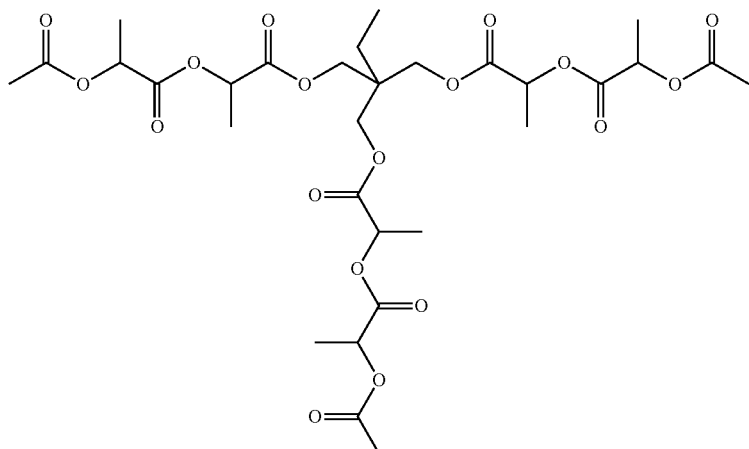

[Chemical Formula 3]

The PLA resin, which is a cyclic resource material having excellent biodegradability, may have properties somewhere between polyethylene terephthalate (PET) resin and polyamide (PA) resin, and may be prepared through direct polycondensation of lactic acid or through ring-opening polymerization (ROP) of lactide.

The lactic acid and lactide have L-form, D-form, and meso-form isomers and have properties in which crystallinity, melting points, mechanical properties and the like may vary depending on composition. Specifically, an L-lactide polymer is more crystalline than an amorphous D-form polymer and has more excellent mechanical properties than the D-form polymer as the L-lactide polymer is crystalline.

The PLA resin is an environmentally friendly resin material and is used in various fields. However, the PLA resin is easily degraded when heated at high temperature for a long time. The PLA resin has low workability, and, after processed, has low flexibility, is easily crashed, and has low impact resistance. To overcome its drawbacks, the PLA resin requires improved workability, flexibility and durability by a reduction in contact between molecules in the resin using a plasticizer.

An ideal environmentally friendly plasticizer has to be prepared using a recyclable raw material, and has to have biodegradability. Additionally, it has to have excellent compatibility with a resin like an existing plasticize and, when processed, has to have excellent chemical stability and exudation resistance.

Research into environmentally friendly plasticizers such as a vegetable oil-based environmentally friendly plasticizer, a succinic acid-based environmentally friendly plasticizer, an isosorbide plasticizer and the like has been so far performed. However, unlike an existing phthalate-based plasticizer, they have limited physical properties.

Against this back drop, a plasticizer is prepared through ring-opening polymerization of D,L-lactide, thereby ensuring excellent compatibility between the plasticizer and a PLA resin, and is prepared through acetylation by which a hydroxy group of the terminal of the plasticizer is replaced with an acetyl group, thereby increasing temperature of thermal decomposition. Additionally, the plasticizer has more excellent elongation and tensile strength than a commercial plasticizer through acetylation, thereby ensuring improved physical properties.

A PLA resin composition containing the exemplary plasticizer may be prepared using a method well-known to those in the art. "For example, the method may include a method by which a plasticizer is added to a PLA resin the molecular weight is increased through the process of cross-linking or hardening, or a method by which a plasticizer is added to a precursor in the form of an oligomer and then hardened.

An exemplary PLA resin composition may contain any one selected from the acetylated lactide oligomer-based plasticizers expressed as the above-described chemical formulas 1 to 3 in a range of 25 to 70 phr with respect to a PLA resin composition. The amount of the acetylated lactide oligomer-based plasticizer according to the present disclosure may be properly increased and decreased on the basis of use of the resin composition. When less than 25 phr of the acetylated lactide oligomer-based plasticizer is added, flexibility or workability revealed by the plasticizer may not be ensured, and, when more than 70 phr of the acetylated lactide oligomer-based plasticizer is added, required mechanical properties and exudation resistance may not be ensured. Accordingly, the above-described range may be preferable.

The exemplary PLA resin composition may have more excellent thermal stability and excellent physical properties such as tensile strength, elongation and modulus elasticity and glass transition temperature than a resin composition to which a commercial plasticizer of the related art is added.

Thus, when plastics are manufactured using a PLA resin composition containing the exemplary plasticizer, they may have excellent tensile strength and low glass transition temperature, and may be easily formed into a film. Additionally, they may maintain flexibility at low temperature and may be processed as a flexible product such as a film or an artificial leather sheet. When containing the exemplary plasticizer, plastics may have excellent compatibility with a PLA resin, may not cause bleeding, and may have excellent thermal stability, thereby enabling an extended lifespan of a film, a sheet and the like that are manufactured using the PLA resin.

Embodiment

Below, embodiments are provided to specifically describe the present disclosure. However, the embodiments may be modified in various different forms, and the present disclosure should not be construed as being limited to the below-described embodiments. The embodiments are provided to completely describe the disclosure to one having ordinary skill in the art.

<Embodiment 1> Preparation for Acetylated Lactide Oligomer-Based Plasticizer (LO-1Ac)

Into a pressure vessel, 100 g (0.69 mol) of D, L-lactide, and 20.2 mL (0.35 mol) of ethanol as an initiator were put. As a catalyst, 0.9 mmol of $Sn(Oct)_2$ was added, ring-opening polymerization of lactide was performed at 110° C. for four hours without using an additional solvent, and then a lactide oligomer (LO-1) was synthesized.

Acetic anhydride was put into the synthesized lactide oligomer (LO-1) and then was acetylated at 100° C. for 42 hours, and, after a hydroxy group was observed disappearing using an NMR, the reaction was finished. When the reaction was finished, temperature of an outcome was decreased to room temperature, acetic acid and unreacted acetic anhydride were removed in a vacuum state, and then an acetylated lactide oligomer-based plasticizer (LO-1Ac) was obtained.

<Embodiment 2> Preparation for Acetylated Lactide Oligomer-Based Plasticizer (LO-2Ac)

As an initiator, 32.9 mL (0.35 mol) of diethylene glycol (DEG) was used, and ring-opening polymerization of lactide was performed using the same method as in embodiment 1, and then a lactide oligomer (LO-2) was sythesized.

The synthesized lactide oligomer (LO-2) was acetylated using the same method as in embodiment 1, and an acetylated lactide oligomer-based plasticizer (LO-2Ac) was obtained.

<Embodiment 3> Preparation for Acetylated Lactide Oligomer-Based Plasticizer (LO-3Ac)

As an initiator, 46 g (0.35 mol) of 1,1,1-tris(hydroxymethyl)propane (TMP) was used, and ring-opening polymerization of lactide was performed using the same method as in embodiment 1, and then a lactide oligomer (LO-3) was synthesized.

The synthesized lactide oligomer (LO-3) was acetylated using the same method as in embodiment 1, and an acetylated lactide oligomer-based plasticizer (LO-3Ac) was obtained.

<Experimental Example 1> Analysis of Structure of Acetylated Lactide Oligomer-Based Plasticizer Structures of the acetylated lactide oligomer-based plasticizers (LO-1Ac, LO-2Ac, and LO-3Ac) prepared according to embodiments 1 to 3, and lactide oligomer plasticizers (LO-1, LO-2, and LO-3) prior to acetylation were compared and analyzed.

FIG. 2 is a graph illustrating results of comparison of $^1$H-NMR before and after acetylation of a hydroxy group terminal of a lactide oligomer according to embodiment 1, FIG. 3 is a graph illustrating results of comparison of $^1$H-NMR before and after acetylation of a hydroxy group terminal of a lactide oligomer according to embodiment 2, and FIG. 4 is a graph illustrating results of comparison of $^1$H-NMR before and after acetylation of a hydroxy group terminal of a lactide oligomer according to embodiment 3.

Referring to FIGS. 2 to 4, two lactide monomers per a single initiator were ring-opening polymerized in the form of an oligomer (LO) through calculation of molecular weight as a result of $^1$H-NMR analysis. Then a terminal of the oligomer and hydrogen peak of a hydroxy group disappeared, and methyl hydrogen peak of an acetyl group of the terminal was generated through acetylation. All the plasticizers had molecular weight similar to actual molecular weight and were synthesized with a high conversion rate.

FIG. 5 is a graph illustrating results of comparison of MALDI-TOF-MS before and after acetylation of a hydroxy group terminal of a lactide oligomer according to embodiment 1, FIG. 6 is a graph illustrating results of comparison of MALDI-TOF-MS before and after acetylation of a hydroxy group terminal of a lactide oligomer according to embodiment 2, and FIG. 7 is a graph illustrating results of comparison of MALDI-TOF-MS before and after acetylation of a hydroxy group terminal of a lactide oligomer according to embodiment 3.

Referring to FIGS. 5 to 7, a gap of 144 Da at a major peak was shown with respect to molar mass corresponding to a lactide unit as a result of MALDI-TOF-MS measurement. Molar mass matched the molecular weight of the lactide monomer. Additionally, the lactide was expressed as two 72 Da repetitive units while ring-opening polymerization occurred. Accordingly, on the graph, a gap of 72 Da was shown. Thus, molecular weight increased by as much as a change in the terminal through acetylation.

A formula such as (molecular weight of an initiator)+(molecular eight of a monomer)×(the number of polymerized monomers)+(molecular weight of ions used for an analysis in a matrix) was used to calculate molecular weight of the plasticizers. Thus, distribution of an oligomer in which approximately three to seven monomers were polymerized was confirmed.

<Experimental Example 2> Thermal Properties of Acetylated Lactide Oligomer-Based Plasticizer As a resin is generally processed at high temperature, thermal stability of a plasticizer is an important factor. Thermal stability of the acetylated lactide oligomer-based plasticizers (LO-1Ac, LO-2Ac, and LO-3Ac) prepared according to embodiments 1 to 3, and thermal stability of a bis(2-ethylhexyl) adipate (DOA) plasticizer and an acetyl tributyl citrate (ATBC) plasticizer in the market were evaluated.

<2-1> Results of Thermogravimetric Analysis (TGA)

In thermogravimetric analysis (TGA), a Q-5000 of TA was used to measure temperature of thermal decomposition of the plasticizers. Under the nitrogen atmosphere, temperature of 10 to 30 mg of a sample was increased up to 25 to 600° C. at a speed of 10° C./min to measure a change in mass of the sample.

FIG. 8 is a graph illustrating results of comparison of analyses of plasticizers of embodiments 1 to 3 and analyses of DOA and ATBC plasticizers using thermogravimetric analysis (TGA).

Referring to FIG. 8, thermal decomposition of all the plasticizers occurred in a single mechanism according to results of a thermal decomposition curve of TGA. The DOA and ATBC plasticizers all decomposed at about 200° C., and the LO-Ac plasticizer decomposed even at 200° C. or higher. Additionally, in the case of the LO-Ac plasticizer, thermal decomposition occurred at higher temperature as LO-1Ac, LO-2Ac, and LO-3Ac has more branches in order.

<2-2> Measurement of Glass Transition Temperature (Tg)

Temperatures of 10~30 mg of samples of the plasticizers of embodiments 1 to 3, and DOA and ATBC plasticizers were increased up to −80 to 200° C. at a speed of 10° C./min under the nitrogen atmosphere, A Q-20 of TA was used to measure a change in mass of the samples.

FIG. 9 is a graph illustrating results of comparison of evaluations of thermal properties of plasticizers of embodiments 1 to 3 and evaluations of thermal properties of DOA and ATBC plasticizers using differential scanning calorimetry (DSC).

Referring to FIG. 9, a change in glass transition temperatures of an oligomer according to acetylation had nothing to do with a structure of an initiator. However, a low glass transition temperature suggested that the plasticizer was in the phase of liquid with low viscosity.

<2-3> Measurement of 5% Weight Loss Temperature (Decomposition Temperature; $T_{d,5\%}$)

Temperatures of 10~30 mg of samples of the plasticizers of embodiments 1 to 3, and the plasticizers of comparative examples 1 and 2 were increased up to 25 to 600° C. at a speed of 10° C./min under the nitrogen atmosphere. A Q-20 of TA was used to measure a change in mass of the samples.

TABLE 1

| | $T_{d,5\%}$ (° C.) | $\Delta T_{d,5\%}$ (° C.) | $T_g$ (° C.) |
|---|---|---|---|
| LO-1 | 108 | +49 | −43 |
| LO-1Ac | 155 | | −28 |
| LO-2 | 196 | +29 | −35 |
| LO-2Ac | 225 | | −32 |
| LO-3 | 220 | +39 | −18 |
| LO-3Ac | 259 | | −25 |
| DOA | 205 | — | — |
| ATBC | 217 | — | — |

Table 1 shows 5% weight loss temperature and glass transition temperature of acetylated lactide oligomer-based plasticizers (LO-1 Ac, LO-2Ac, and LO-3Ac), lactide oligomer plasticizers (LO-1, LO-2, and LO-3) prior to acetylation, and DOA and ATBC plasticizers.

Referring to Table 1, 5% weight loss temperatures ($T_{d,5\%}$) were increased in the order of LO-1Ac<DOA<ATBC<LO-2AC<LO-3AC. This indicates that 5% weight loss temperatures of LO-2Ac and LO-3Ac were similar to or higher than a 5% weight loss temperature of 205° C. of DOA and a 5% weight loss temperature of 217° C. of ATBC.

Thus, the LO-Ac plasticizer may be processed at a higher temperature than an existing plasticizer. This is because a hydroxy group of the terminal of the LO-Ac plasticizer was protected by an acetyl group and trans-esterification caused by a back-biting reaction of a lactide oligomer did not occur.

<Embodiment 4> Preparation for PLA Sample Including Acetylated Lactide Oligomer-Based Plasticizer (LO-1Ac)

First, 10, 25, and 65 phr (part per hundred resin) of the LO-1Ac plasticizer of embodiment 1 were respectively added to a PLA resin and prepared as 10%(iv) of a solution using chloroform. The solution was agitated for more than one day until it was completely melted; was poured on a perfluoroalkoxy (PFA) watch dish, and then dried at room temperature for 72 hours and dried in a vacuum oven at 70° C. for 24 hours using the solvent-casting method. Then the dried solvent was cut into pieces, was mixed at 200° C. for three minutes using a micro compounder and was injected. Thus, a PLA sample was prepared.

<Embodiment 5> Preparation for PLA Sample Including Acetylated Lactide Oligomer-Based Plasticizer (LO-2Ac)

A PLA sample was prepared using the same method as embodiment 4, except that 10, 25, and 65 phr of the LO-2Ac plasticizer of embodiment 2 were respectively added to a PLA resin.

<Embodiment 6> Preparation for PLA Sample Including Acetylated Lactide Oligomer-Based Plasticizer (LO-3Ac)

A PLA sample was prepared using the same method as embodiment 4, except that 10, 25, and 65 phr of the LO-3Ac plasticizer of embodiment 3 were respectively added to a PLA resin.

<Comparative Example 1> Preparation for PLA Sample Including Adipate-Based Plasticizer (DOA)

A PLA sample was prepared using the same method as embodiment 4, except that 10, 25, and 65 phr of a bis(2-ethylhexyl) adipate (DOA) plasticizer, which is a petroleum-based adipate-based plasticizer, were respectively added to a PLA resin.

<Comparative Example 2> Preparation for PLA Sample Including Citric Acid-Based Plasticizer (ATBC)

A PLA sample was prepared using the same method as embodiment 4, except that 10, 25, and 65 phr of an acetyl tributyl citrate (ATBC) plasticizer, which is a citric acid-based plasticizer, were respectively added to a PLA resin.

<Experimental Example 3> Evaluation of Plasticity of Acetylated Lactide Oligomer-Based Plasticizer <3-1> Measurement of Tensile Strength (MPa) and Elongation (%)

A PLA sample was manufactured in the form of a microtensile bar (ASTM D1708), and a universal testing machine (UTM, Instron 5567) and a 1000N load cell sensor were used to measure tensile strength (σ, stress at break) and elongation (ε, strain at break) of PLA film samples of embodiments 4 to 6, and comparative examples 1 and 2, under conditions of room temperature and speed of 10 mm/min.

FIG. 10 is a graph illustrating results of comparison of stress-strain curves of embodiments 4 to 6 in which 10 phr of a plasticizer was added, a PLA sample of comparative examples 1 and 2 in which 10 phr of a plasticizer was added, and a PLA sample in which a plasticizer was not added, FIG. 11 is a graph illustrating results of comparison of stress-strain curves of embodiments 4 to 6 in which 25 phr of a plasticizer was added, a PLA sample of comparative examples 1 and 2 in which 25 phr of a plasticizer was added, and a PLA sample in which a plasticizer was not added, and FIG. 12 is a graph illustrating results of comparison of stress-strain curves of embodiments 4 to 6 in which 65 phr of a plasticizer was added, a PLA sample of comparative examples 1 and 2 in which 65 phi of a plasticizer was added, and a PLA sample in which a plasticizer was not added.

In general, mechanical strength of a material according to an interaction between polymer chains may be determined using tensile strength of the material. A yielding point denotes stress of a point at which a high elongation percentage is shown on the stress-strain curves without an increase in stress, or denotes a value at which a maximum load is divided by a cross section of a circle when a high elongation percentage is shown on the stress-strain curves without an increase in stress. The yielding point denotes a point at which an object to which force is applied may no longer return to its primary state.

Additionally, in case strain applied to an elastic object is referred to as tensile strength ($\sigma$), and that strain in a lengthwise direction is referred to as $\varepsilon$, Young's modulus E is expressed as $E=\sigma/\varepsilon$. When E of a material is high, the material is solid, hardly compressed and has high restoring force.

Referring to FIGS. 10 to 12, when a PLA sample contained no plasticizer, tensile strength (71.6 MPa) was high, and a yielding point was not observed. This is because a polymer is easily crashed due to cohesiveness of a polymer chain. However, when a PLA sample contained a plasticizer, ductility was increased and a yielding point was observed. This is because an interaction between polymer chains in a PLA sample is weaken through a blend of a plasticizer and the PLA sample, tensile strength is decreased, tensile elongation is increased, and flexibility and mobility of the polymerchains are improved.

When 10 phr of a plasticizer were added in embodiments 4 to 6, and in comparative examples 1 and 2, the amount of the plasticizer was not enough. Accordingly, liquidity of polymer chains was not increased. When a DOA plasticizer was added in comparative example 1, the phenomena of cavitation and crazing occurred as compatibility between the DOA plasticizer and PLA was low.

However, when 25 phr of a plasticizer was added, tensile elongation of a sample mixed with the LO-Ac plasticizer of embodiments 4 to 6 was highest, and Young's modulus thereof was smallest, Performance of the LO-Ac plasticizer was more excellent than that of the plasticizers of comparative example 1.

<3-2> Measurement of Storage Modulus (G') and Tan Delta (Tan $\delta$)

To measure dynamic and mechanical properties of a soft-nitrided PLA sample, a Q-800 dynamic mechanical analyzer of TA was used. While temperature of a rectangle-shaped sample (20 mm×5.3 mm×1 mm) was raised from −100° C. up to 100° C. at a speed of 3° C./min, storage modulus (G') and Tan delta(Tan $\delta$) of the PLA sample were obtained as a function of temperature.

Tan $\delta$ (tangent delta) denotes a ratio of lost modulus of elasticity to stored modulus of elasticity and is used to measure viscoelasticity of a polymer. In general, when plasticizer content becomes higher, storage modulus becomes lower, and a peak temperature of Tan $\delta$ is decreased.

Dynamic and mechanical properties and vales of glass transition temperature of a sample were measured through DMA analysis.

FIG. 13 is a graph illustrating results of comparison of storage modulus (G') of embodiments 4 to 6 in which 10 phr of a plasticizer was added, storage modulus (G') of a PLA sample of comparative examples 1 and 2 in which 10 phr of a plasticizer was added, and storage modulus (G') of a PLA sample in which a plasticizer was not added, FIG. 14 is a graph illustrating results of comparison of storage modulus (G') of embodiments 4 to 6 in which 25 phr of a plasticizer was added, storage modulus (G') of a PLA sample of comparative examples 1 and 2 in which 25 phi of a plasticizer was added, and storage modulus (G') of a PLA sample in which a plasticizer was not added, and FIG. 15 is a graph illustrating results of comparison of storage modulus (G') of embodiments 4 to 6 in which 65 phr of a plasticizer was added, storage modulus (G') of a PLA sample of comparative examples 1 and 2 in which 65 phr of a plasticizer was added, and storage modulus (G') of a PLA sample in which a plasticizer was not added.

FIG. 16 is a graph illustrating results of comparison of tan $\delta$ of embodiments 4 to 6 in which 10 phr of a plasticizer was added, tan $\delta$ of a PLA sample of comparative examples 1 and 2 in which 10 phr of a plasticizer was added, and tan $\delta$ of a PLA sample in which a plasticizer was not added, FIG. 17 is a graph illustrating results of comparison of tan $\delta$ of embodiments 4 to 6 in which 25 phr of a plasticizer was added, tan $\delta$ of a PLA sample of comparative examples 1 and 2 in which 25 phi of a plasticizer was added, and tan $\delta$ of a PLA sample in which a plasticizer was not added, and FIG. 18 is a graph illustrating results of comparison of tan $\delta$ of embodiments 4 to 6 in which 65 phr of a plasticizer was added, tan $\delta$ of a PLA sample of comparative examples 1 and 2 in which 65 phr of a plasticizer was added, and tan $\delta$ of a PLA sample in which a plasticizer was not added.

FIG. 19 is a graph illustrating results of comparison of analyses of embodiments 4 to 6 in which 10 phr of a plasticizer was added, a PLA sample of comparative examples 1 and 2 in which 10 phi of a plasticizer was added, and a PLA sample in which a plasticizer was not added, using differential scanning calorimetry (DSC), FIG. 20 is a graph illustrating results of comparison of analyses of embodiments 4 to 6 in which 25 phi of a plasticizer was added, a PLA sample of comparative examples 1 and 2 in which 25 phi of a plasticizer was added, and a PLA sample in which a plasticizer was not added, using differential scanning calorimetry (DSC), and FIG. 21 is a graph illustrating results of comparison of analyses of embodiments 4 to 6 in which 65 phr of a plasticizer was added, a PLA sample of comparative examples 1 and 2 in which 65 phr of a plasticizer was added, and a PLA sample in which a plasticizer was not added, using differential scanning calorimetry (DSC).

Referring to FIGS. 13 to 21, when 10 phi of a plasticizer was added, the amount of the plasticizer was not enough. Accordingly, there was almost no decrease in the glass transition temperature at which physical properties are changed from properties of a glass phase into properties of a rubber phase. When 25 phr of the ATBC plasticizer of comparative example 2 was added, storage modulus of the PLA sample started to be reduced at around room temperature, and the PLA sample started to flow at 60° C. or higher. When the DOA plasticizer of comparative example 1 was used, glass transition of the PLA sample started at around 40° C. When the LO-AC plasticizer of embodiments 4 to 6 were used, glass transition of the PLA sample started at around 30 and the PLA sample started to flow at around 70 to 80° C.

When 65 phr of a plasticizer was added to a PLA sample, properties of the plasticizer were markedly revealed. When the LO-Ac plasticizers of embodiments 4 to 6 were used, storage modulus of the PLA sample was maintained, and then glass transition of the PLA sample started at around room temperature and the PLA sample started to flow at around 60° C. When the DOA plasticizer of comparative example 1 and the ATBC plasticizer of comparative example 2 were added, storage modulus was reduced rather than maintained. Specifically, Tan δ peak of the ATBC plasticizer of comparative example 2 had a shape with a wide width, and another peak appeared in low-temperature sections.

When a polymer complex has excellent compatibility, the polymer complex generally has a single glass transition temperature. Accordingly, as the ATBC plasticizer has a limited miscibility, glass transition temperature (Tg) in an area with a large amount of a plasticizer and glass transition temperature (Tg) in an area with a large amount of a PLA resin varied.

Thus, the PLA resin composition according to the present disclosure had more excellent thermal stability and more excellent physical properties such as tensile strength, elongation, modulus of elasticity and glass transition temperature than a resin composition that contains a commercial plasticizer.

When manufactured using a PLA resin composition containing the plasticizer of the present disclosure, plastics may have excellent tensile strength and low glass transition temperature, may be easily formed into a film, may maintain flexibility at low temperature and may be readily processed as a flexible product such as a film or an artificial leather sheet. When containing the plasticizer of the present disclosure, plastics may have excellent compatibility with a PLA resin, may not cause bleeding, and may have excellent thermal stability, thereby enabling an extended lifespan of a film, a sheet and the like that are manufactured using the PLA resin.

The acetylated lactide oligomer-based plasticizer, method of preparing the same and PLA resin composition containing the same have been described with reference to their embodiments. However, it will be apparent that various modifications may be made within the scope of the present disclosure.

Thus, the present disclosure should not be limited to the embodiments set forth herein. Rather, the present disclosure should be defined according to the appended claims and equivalents thereof.

The above-described embodiments are provided only as examples. Accordingly, the embodiments should not be interpreted as limiting the disclosure. Further, the scope of the disclosure is defined according to the appended claims rather than the detailed description. Furthermore, all the modifications and modified forms drawn from the meanings and scopes of the claims and the equivalents thereof should be interpreted as being included in the scope of the present disclosure.

What is claimed is:

1. A method of preparing an acetylated lactide oligomer-based plasticizer, comprising:
   (a) synthesizing a lactide oligomer through ring-opening polymerization (ROP) of an initiator and lactide, wherein the initiator is 1,1,1-tris(hydroxymethyl)propane or diethylene glycol;
   (b) putting acetic anhydride into the lactide oligomer and performing acetylation; and
   (c) removing acetic acid generated in step (b) and unreacted acetic anhydride.

2. The method of claim 1, wherein step (a) is carried out at 100 to 120° C. for two to six hours.

3. The method of claim 1, wherein, in step (a), a catalyst of the ring-opening polymerization includes tin(II) 2-ethylhexanoate.

4. The method of claim 1, wherein step (b) is carried out at 80 to 120° C. for 40 to 60 hours.

5. An acetylated lactide oligomer-based plasticizer, which is manufactured by acetylating a lactide oligomer synthesized through ring-opening polymerization (ROP) of an initiator and lactide, is expressed as any one of following chemical formulas 2 to 3:

[Chemical formula 2]

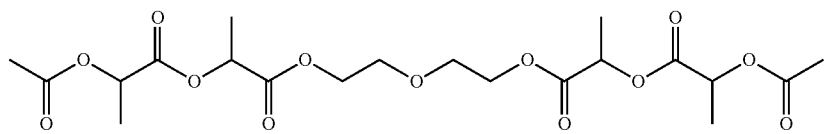

[Chemical formula 3]

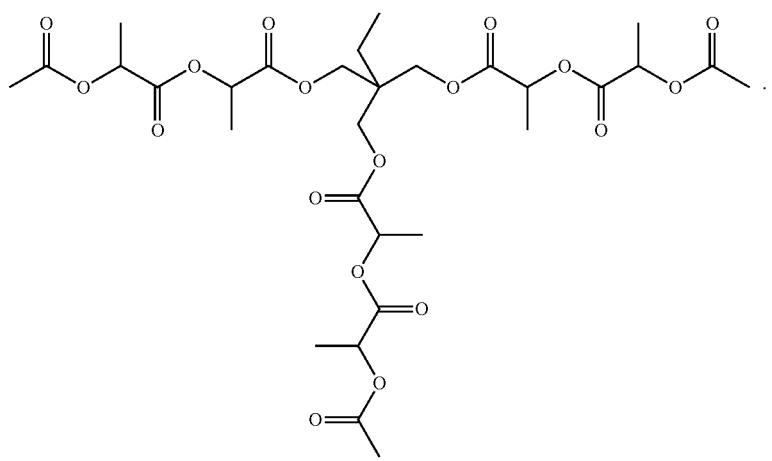

6. The acetylated lactide oligomer-based plasticizer of claim 5, wherein the initiator is 1,1,1-tris(hydroxymethyl) propane or diethylene glycol.

7. The acetylated lactide oligomer-based plasticizer of claim 5, wherein a catalyst of the ring-opening polymerization includes tin(II) 2-ethylhexanoate.

8. The acetylated lactide oligomer-based plasticizer of claim 5, wherein the ring-opening polymerization is carried out at 100 to 120° C. for two to six hours.

9. The acetylated lactide oligomer-based plasticizer of claim 5, wherein the acetylation is carried out at 80 to 120° C. for 40 to 60 hours.

10. A poly lactic acid (PLA) resin composition, comprising:
a poly lactic acid (PLA) resin and any one selected from acetylated lactide oligomer-based plasticizers expressed as following chemical formulas 2 to 3:

[Chemical formula 2]

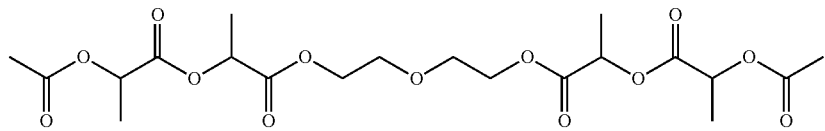

[Chemical formula 3]

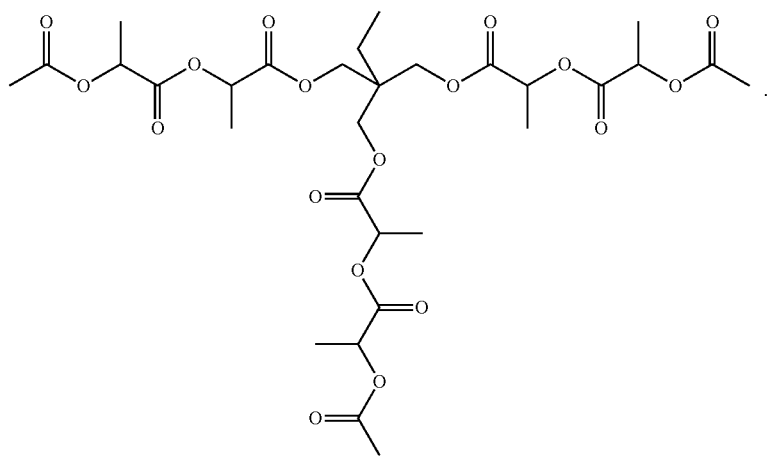

11. The PLA resin composition of claim 10, wherein the plasticizer is contained in a range of 25 to 70 phr with respect to the PLA resin composition.

* * * * *